United States Patent
Godavarty et al.

(10) Patent No.: US 10,258,242 B2
(45) Date of Patent: Apr. 16, 2019

(54) NEAR-INFRARED OPTICAL IMAGING SYSTEM FOR HEMODYNAMIC IMAGING, PULSE MONITORING, AND MAPPING SPATIO-TEMPORAL FEATURES

(71) Applicants: Anuradha Godavarty, Miami, FL (US); Youngjin Jung, Miami, FL (US)

(72) Inventors: Anuradha Godavarty, Miami, FL (US); Youngjin Jung, Miami, FL (US)

(73) Assignee: THE FLORIDA INTERNATIONAL UNIVERSITY BOARD OF TRUSTEES, Miami, FL (US)

( * ) Notice: Subject to any disclaimer, the term of this patent is extended or adjusted under 35 U.S.C. 154(b) by 757 days.

(21) Appl. No.: 14/590,703

(22) Filed: Jan. 6, 2015

(65) Prior Publication Data
US 2015/0190061 A1 Jul. 9, 2015

Related U.S. Application Data

(60) Provisional application No. 61/924,049, filed on Jan. 6, 2014.

(51) Int. Cl.
*A61B 5/1455* (2006.01)
*A61B 5/02* (2006.01)
(Continued)

(52) U.S. Cl.
CPC ........ *A61B 5/02028* (2013.01); *A61B 5/0059* (2013.01); *A61B 5/02416* (2013.01);
(Continued)

(58) Field of Classification Search
None
See application file for complete search history.

(56) References Cited

U.S. PATENT DOCUMENTS 5,730,133 A 3/1998 Godik
5,830,145 A 11/1998 Tenhoff
(Continued)

FOREIGN PATENT DOCUMENTS

DE 102005058598 7/2006
EP 1797818 A2 6/2007
(Continued)

OTHER PUBLICATIONS

Search Report for International application No. PCT/US2015/010300, dated Jun. 24, 2015.
(Continued)

*Primary Examiner* — Eric Winakur
*Assistant Examiner* — Marjan Fardanesh
(74) *Attorney, Agent, or Firm* — Marshall, Gerstein & Borun LLP

(57) ABSTRACT

The present application describes techniques to image biological tissue to determine biological information of an imaged tissue sample such as changes in hemoglobin concentrations, blood flow rate (pulse), and/or spatio-temporal features. Embodiments include illuminating the tissue sample with light in the near-infrared (NIR) spectrum, which is minimally absorbed but scattered through the tissue sample. By detecting the NIR light that is attenuated through, transmitted through, and/or reflected off the tissue to be imaged, the resulting NIR intensity signals may be further analyzed to provide this data. Embodiments include using multiple NIR light sources having varying wavelengths to obtain changes in the oxy- and deoxy-hemoglobin concentrations of the imaged tissue region. The tissue sample may be imaged over a time period, and the NIR images may be viewed statically or in real time after post-processing analyses have been performed.

37 Claims, 9 Drawing Sheets

(51) Int. Cl.
  *A61B 5/024* (2006.01)
  *A61B 5/06* (2006.01)
  *A61B 5/00* (2006.01)
  *G01J 3/28* (2006.01)
  *G01J 3/02* (2006.01)
  *G01J 3/10* (2006.01)
  *G01N 21/31* (2006.01)

(52) U.S. Cl.
  CPC .......... *A61B 5/065* (2013.01); *A61B 5/14551* (2013.01); *A61B 5/7207* (2013.01); *A61B 5/742* (2013.01); *G01J 3/0264* (2013.01); *G01J 3/0272* (2013.01); *G01J 3/108* (2013.01); *G01J 3/2823* (2013.01); *A61B 2560/0431* (2013.01); *G01N 2021/3155* (2013.01); *G01N 2201/0221* (2013.01)

(56) References Cited

U.S. PATENT DOCUMENTS

| | | | |
|---|---|---|---|
| 5,971,997 | A | 10/1999 | Guthrie et al. |
| 5,983,122 | A | 11/1999 | Jarman et al. |
| 6,795,195 | B1 | 9/2004 | Barbour et al. |
| 6,808,289 | B2 | 10/2004 | Reed |
| RE38,800 | E | 9/2005 | Barbour |
| 8,070,682 | B2 | 12/2011 | Zhu |
| 8,712,504 | B2 | 4/2014 | Godavarty et al. |
| 2002/0035317 | A1 | 3/2002 | Cheng et al. |
| 2002/0045811 | A1 | 4/2002 | Kittrell et al. |
| 2002/0050988 | A1 | 5/2002 | Petrov et al. |
| 2004/0215072 | A1 | 10/2004 | Zhu |
| 2004/0254464 | A1 | 12/2004 | Stribling |
| 2005/0004453 | A1 | 1/2005 | Tearney et al. |
| 2005/0116179 | A1 | 6/2005 | Aguirre et al. |
| 2007/0219450 | A1 | 9/2007 | Azar et al. |
| 2008/0294056 | A1 | 11/2008 | Boutet et al. |
| 2009/0137908 | A1 | 5/2009 | Patwardhan |
| 2009/0240145 | A1 | 9/2009 | Otsuka |
| 2009/0306521 | A1 | 12/2009 | Ermakov et al. |
| 2010/0010340 | A1 | 1/2010 | Godavarty et al. |
| 2010/0078576 | A1 | 4/2010 | Ntziachristos et al. |
| 2010/0155599 | A1 | 6/2010 | Godavarty et al. |
| 2010/0256496 | A1 | 10/2010 | Zhu |
| 2010/0324423 | A1 | 12/2010 | El-Aklouk et al. |
| 2011/0190639 | A1 | 8/2011 | Peltie et al. |
| 2011/0229840 | A1 | 9/2011 | Liang et al. |
| 2012/0271129 | A1 | 10/2012 | Wang |
| 2013/0090541 | A1 | 4/2013 | MacFarlane et al. |
| 2013/0109941 | A1 | 5/2013 | Li et al. |
| 2013/0169759 | A1 | 7/2013 | Godavarty et al. |
| 2014/0364743 | A1 | 12/2014 | Godavarty et al. |

FOREIGN PATENT DOCUMENTS

| | | |
|---|---|---|
| EP | 2 319 406 A1 | 5/2011 |
| WO | WO-94/24927 A1 | 11/1994 |
| WO | WO-99/24927 A1 | 5/1999 |
| WO | WO-2008/039988 A2 | 4/2008 |
| WO | WO-2011/156810 A2 | 12/2011 |
| WO | WO-2015103614 A2 | 7/2015 |

OTHER PUBLICATIONS

Written Opinion for International application No. PCT/US2015/010300, dated Jun. 24, 2015.
International Preliminary Report on Patentability issued for PCT Patent Application No. PCT/US2015/010330 dated Jul. 21, 2016.
Extended European Search Report issued in European Pat. Appl. No. 11793309.3 dated Nov. 20, 2015.
Extended European Search Report, European patent application No. EP13733558.4, dated Aug. 7, 2015.
Supplementary Partial European Search Report, European patent application No. EP 11793309, dated Jul. 30, 2015.
Examination Report for European Application No. 11793309.3, dated Jul. 11, 2017.
Partial Supplementary European Search Report for Application No. EP 15733318.8, dated Aug. 18, 2017.
Culver et al., "Three-dimensional diffuse optical tomography in the parallel plane transmission gemoetry: Evaluation of a hybrid frequency domain/continuous wave clinical system for breast imaging", Medical Physics, vol. 30, No. 2, pp. 235-347, 2003.
Ge et al., "A novel optical imager towards breast cancer diagnosis," Medical Physics, vol. 33, No. 6, p. 1989, 2006.
Godavarty et al., "Fluorescence-enhanced optical imaging of large phantoms using single and simultaneous dual point illumination geometries," Medical Physics, vol. 31, No. 2, pp. 183-190, 2004.
International Preliminary Report on Patentability and Written Opinion issued in PCT/US2013/020461 dated Jul. 8, 2014.
International Preliminary Report on Patentability, International Application No. PCT/US2011/040184, dated Dec. 14, 2012.
International Search Report and Written Opinion for International Application No. PCT/US2011/040184, dated Jan. 19, 2012.
International Search Report and Written Opinion, International Application No. PCT/US2013/020461, dated Apr. 29, 2013.
International Search Report for PCT/US2007/079906, dated Feb. 23, 2009.
Jayachandran et al., "Design and development of a hand-held optical probe toward fluorescence diagnostic imaging", Journal of Biomedical Optics, vol. 12, No. 5, pp. 054014-1-054014-10, 2007.
Regalado et al., Automated coregistered imaging using a hand-held probe-based optical imager, Rev. Sci. Instrum., 81:023702 (2010).
Zhu et al., Ultrasound-guided optical tomographic imaging of malignant and benign breast legions: initial clinical results of 19 cases, Neoplasia, 5(5):379-86 (2003).
European patent application No. 15733318.8, Extended European Search Report, dated Nov. 27, 2017.

NEAR-INFRARED OPTICAL IMAGING SYSTEM FOR HEMODYNAMIC IMAGING, PULSE MONITORING, AND MAPPING SPATIO-TEMPORAL FEATURES

CROSS-REFERENCE TO RELATED APPLICATION

This application claims the priority benefit under 35 U.S.C. § 119(e) of U.S. Provisional Patent Application No. 61/924,049, filed Jan. 6, 2014, the disclosure of which is incorporated herein by reference in its entirety.

STATEMENT OF GOVERNMENTAL INTEREST

This invention was made with government support under R15CA119253, awarded by the National Institute of Health (NIH). The Government has certain rights in the invention.

FIELD OF INVENTION

The present disclosure generally relates to systems, methods, apparatus, and non-transitory media for performing medical imaging and, more particularly, to performing hemodynamic imaging, pulse monitoring, and spatio-temporal feature mapping using near-infrared illumination techniques.

BACKGROUND

For patients suffering from a variety of injuries or disease states such as ulcers, wounds caused by amputations, ischemia, peripheral vascular diseases, etc., monitoring a patient's pulse and/or blood flow at or near an afflicted area may provide valuable insight for medical professionals regarding a patient's condition and prognosis.

Traditional methods of performing pulse monitoring, however, include the use of pulse oximeters. But pulse oximeters only provide information regarding a patient's pulse at the extremity in which it is used, such as a patient's finger, for example, and do not provide pulse information at an afflicted area. Pulse oximeters are also limited in that they do not provide information regarding a patient's blood flow or spatio-temporal features.

Furthermore, conventional volumetric blood flow imaging equipment does not typically allow for real-time viewing of hemodynamic data due to the complexity of the processing involved in such measurements. These imaging systems also lack the ability to display information regarding spatio-temporal features, such as how the blood flow changes in one or more portions of a tissue over time.

As a result, portable and non-invasive systems that measure blood flow, pulse, and/or spatio-temporal features present several challenges.

SUMMARY

A near-infrared optical imaging system and method that can be used for hemodynamic imaging, pulse monitoring, and mapping of spatio-temporal features is disclosed. In one embodiment, the system comprises a hand-held optical scanner. The optical scanner provides for a portable, non-invasive imaging system that can monitor the hemodynamic changes within an imaged tissue sample.

The optical system or scanner may be used for applications such as diagnostic, prognostic, preventative screenings, imaging applications, wound healing, monitoring of ulcer treatments, assisting in amputational procedures, sports injuries, ischemia, peripheral vascular diseases, and many other applications. The disclosed optical scanner may act as a visual scope to facilitate the viewing of hemodynamic changes in tissues along with monitoring the pulse of a patient in many areas of the body, beyond the information provided by a typical pulse oximeter. The disclosed optical scanner may act as an analogy to a "visual stethoscope," which can be used in a physician's office, or given its portable nature, may be particularly useful for field use.

Unlike conventional pulse oximeters that obtain pulse information at the tips of the fingers/toes, the disclosed optical imaging system may monitor pulse at the site of blood flow constrictions or regions where there are wounds/ulcers, for example. The disclosed system may non-invasively and, with or without contact, determine the hemodynamic changes found over large tissue areas. The disclosed system may also provide pulse data at several points in the imaged region. Additionally, the optical imaging system may extract spatio-temporal features that can differentiate different tissue types in the imaged regions and show changes in blood flow over time for these different tissue types.

The disclosed optical system may also realign images affected by motion artifacts and extract features from the aligned images for further analysis. Unwanted and/or noisy regions may be removed or masked. Further, the disclosed optical system may extract other tissue information (aside from hemodynamic information) if wavelengths other than those related to hemodynamic information are selected for illumination of a tissue region.

BRIEF DESCRIPTION OF THE DRAWINGS

The following text sets forth a detailed description of numerous different embodiments. However, it should be understood that the detailed description is to be construed as exemplary only and does not describe every possible embodiment since describing every possible embodiment would be impractical. In light of the teaching and disclosure herein, numerous alternative embodiments may be implemented.

It should be understood that, unless a term is expressly defined in this patent application using the sentence "As used herein, the term '_____' is hereby defined to mean . . . " or a similar sentence, there is no intent to limit the meaning of that term, either expressly or by implication, beyond its plain or ordinary meaning, and such term should not be interpreted to be limited in scope based on any statement made in any section of this patent application.

DETAILED DESCRIPTION

According to the embodiments described herein, diffuse optical imaging (DOI) (also termed near infrared spectroscopy (NIRS)) using near-infrared (NIR) light may be used in any suitable imaging application in which hemodynamic imaging, pulse monitoring, and/or mapping of spatio-temporal features is utilized. Some suitable imaging applications may include, for example, functional brain mapping, breast cancer screening, imaging, and/or diagnosis/prognosis, tumor identification, wound imaging, peripheral vascular disease (PVD), peripheral artery disease (PAD) as a preventative diagnostic or prognostic approach, etc. As will be further discussed below, DOI may be implemented as a non-invasive procedure using non-ionizing radiation, utilizes relatively inexpensive instrumentation, and provides functional information from in vivo biological tissues.

DOI may use NIR light between 650-1000 nanometers (nm), as NIR light in this wavelength range is advantageously minimally absorbed and scattered in biological tissues, thus allowing for deep tissue penetration and imaging. DOI implements NIR light that is emitted onto a tissue surface using a NIR source (e.g. laser) and collected at the tissue surface using NIR-sensitive detectors. The difference in optical properties (i.e. absorption and scattering of the NIR light) within the tissue sample may be used to characterize tissues, detect abnormalities, and provide hemodynamic imaging, pulse monitoring, and/or mapping of spatio-temporal features.

Figure 1:
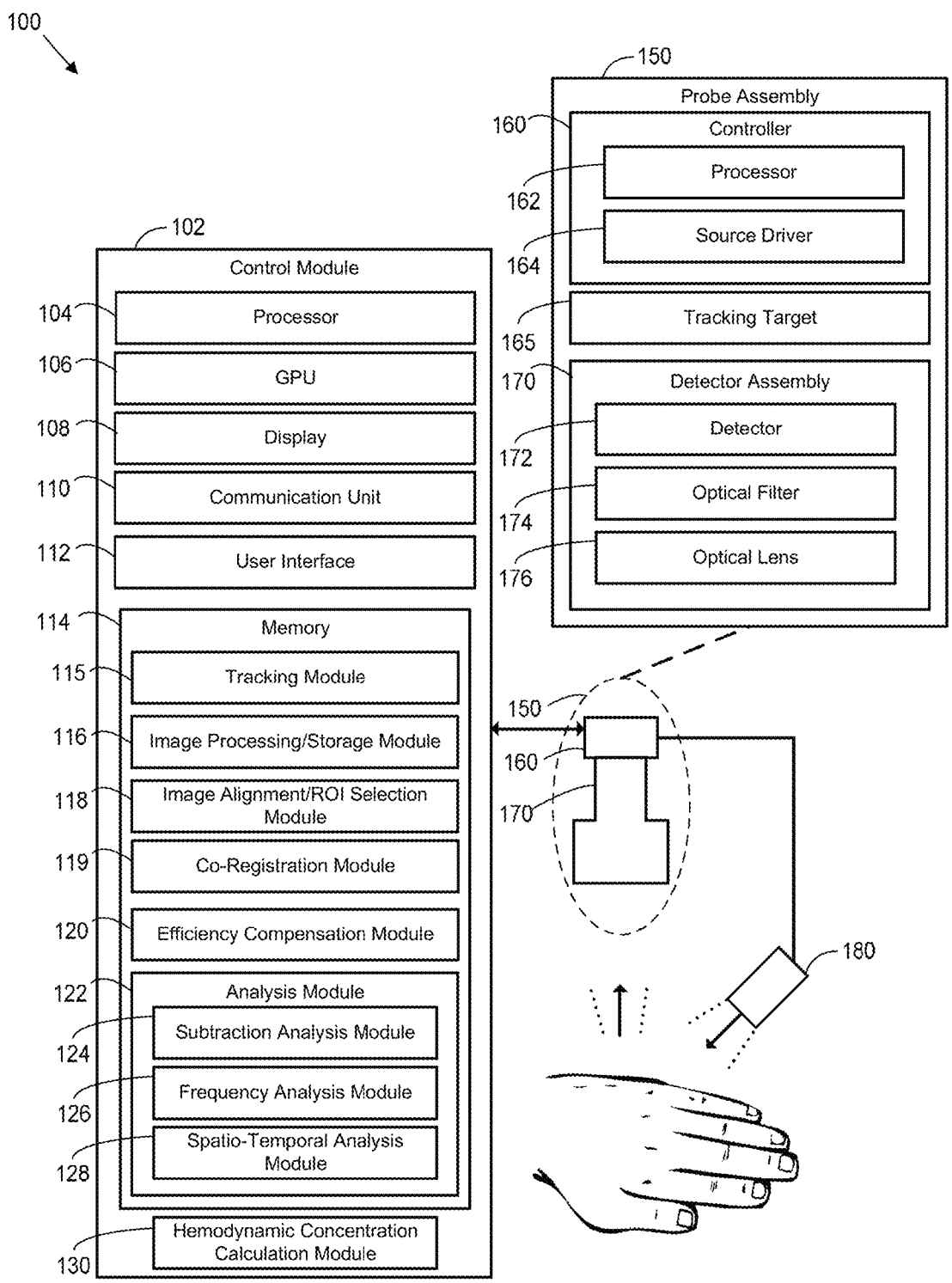
FIG. 1 illustrates a block diagram of an exemplary system 100 in accordance with an exemplary aspect of the present disclosure.

FIG. 1 illustrates a block diagram of an exemplary system 100 in accordance with an exemplary aspect of the present disclosure. System 100 may include a control module 102, a probe assembly 150, and a source assembly 180.

Source assembly 180 may be implemented as any suitable type of light source configured to emit light in the NIR range of wavelengths (e.g., 650-1000 nm) having an appropriate pattern to illuminate a tissue region to be imaged, such as a patient's hand as shown in FIG. 1, for example. Source assembly 180 may include any suitable number and/or type of optics to facilitate the appropriate control of illumination of a tissue region to be imaged, such as lenses, beam expanders, etc.

Source assembly 180 may include any suitable number of light sources configured to emit collimated or non-collimated light in accordance with any suitable number of wavelengths, which may be the same wavelength or different wavelengths as one another. For example, source assembly 180 may include any suitable number (e.g., point sources, arrays, etc.) of light-emitting diodes (LEDs), laser diodes, etc. In some embodiments, source assembly 180 may include a NIR light source that is stationary. In other embodiments source assembly 180 may include a NIR light source that is movable relative to probe assembly 150 to form any suitable number of angles between the NIR light source relative to probe assembly 150.

In an embodiment, source assembly 180 may be configured as a dual-wavelength light source emitting NIR light having wavelengths between the inclusive ranges of 670-710 nm (e.g., 690 nm) and 810-850 (e.g., 830 nm) to obtain the changes in oxy- (HbO) and deoxy-hemoglobin concentrations (HbR) of the imaged tissue region. In some embodiments, source assembly 180 may include a single wavelength light source configured to operate at any suitable number of wavelengths. In other embodiments, source assembly 180 may include any suitable number of light sources, each of which may be configured to operate as the same wavelength as one another or different wavelengths. Because various applications may utilize NIR light of differing wavelengths, source assembly 180 may include one or more modular light sources that may be conveniently interchanged based upon a particular imaging test to be performed.

Probe assembly 150 may have a probe body that may house one or more of a controller 160, a detector assembly 170, a tracking target 165, and/or a source assembly 180. In an embodiment, probe assembly 150 may be implemented as a hand-held and/or portable device. Although FIG. 1 illustrates controller 160 and detector 170 integrated as part of probe assembly 150, probe assembly 150 may house controller 160, tracking target 165, detector assembly 170, and/or source assembly 180. That is, any combination of controller 160, tracking target 165, detector assembly 170, and/or source assembly 180 may be external to, disposed upon, or integrated as part of probe assembly 150.

As NIR light is minimally absorbed and scattered in biological tissues, probe assembly 150 may be configured to facilitate the detection, collection, measurement, and/or processing of NIR light that is emitted by source assembly 180 and attenuated through (adjacent imaging), transmitted through (trans-illumination imaging), and/or reflected off (reflectance imaging), the tissue to be imaged. The NIR light attenuated through, transmitted through, and/or reflected off the tissue sample may be detected by probe assembly 150 to facilitate the imaging process, which is discussed in further detail below. In an embodiment, detector assembly 170 may be configured to capture focused, non-point image samples of biological tissues.

Figure 2:
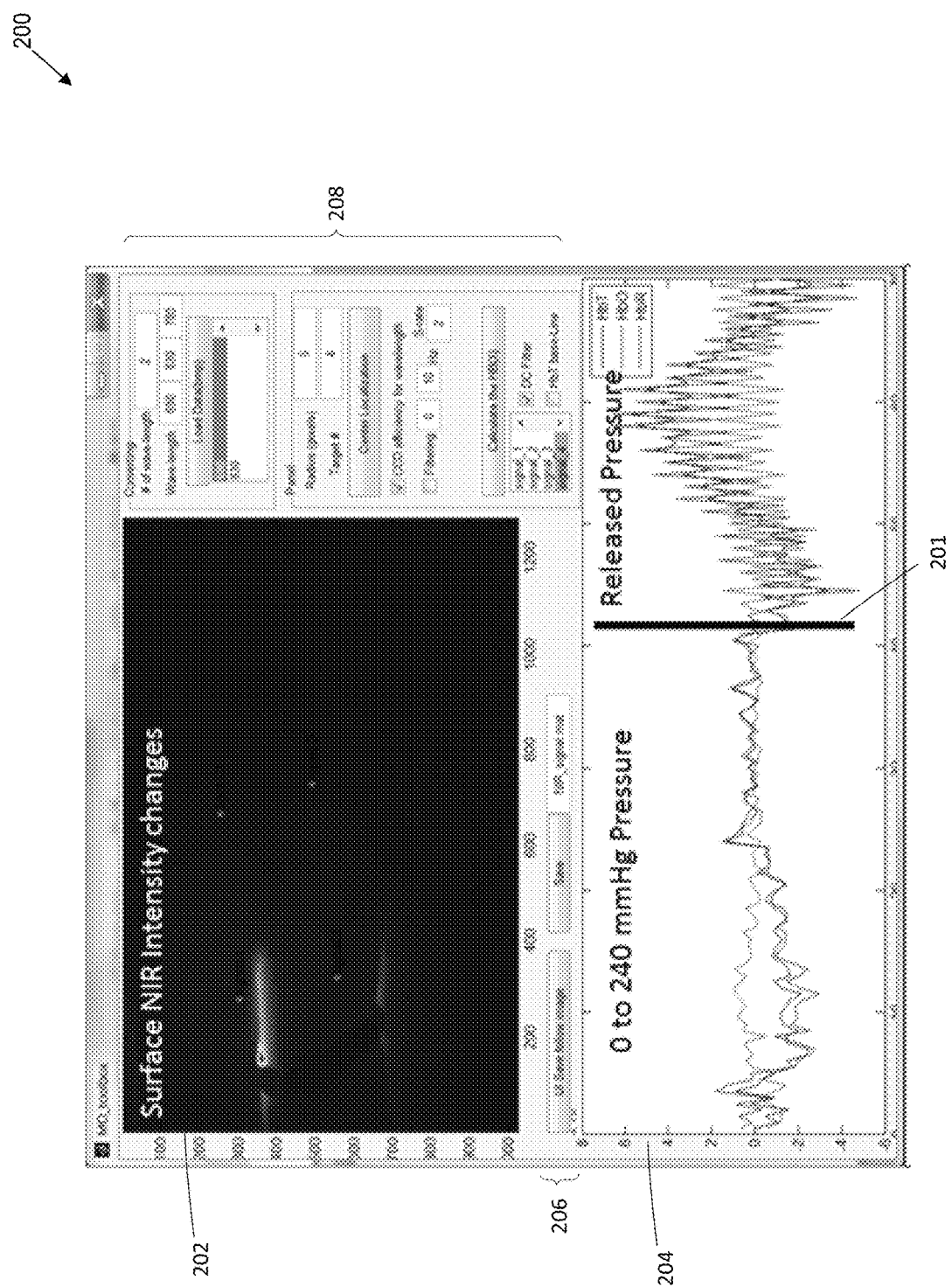
FIG. 2 illustrates an example graphical user interface (GUI) 200 for displaying raw and processed NIR image data in accordance with an exemplary aspect of the present disclosure.

Probe assembly 150 and source assembly 180 may work in conjunction with one another to image the tissue in accordance with any suitable type of imaging mode, such as reflectance, adjacent, or trans-illumination modes, as discussed in the incorporated Provisional Patent Application No. 61/924,049 at page 2, the various modes being illustrated in FIG. 2 therein. For example, source assembly 180 may be positioned adjacent to the biological tissue such that probe assembly 150 is configured to detect NIR light attenuated through the biological tissue (adjacent mode). To provide another example, the biological tissue sample may be positioned between probe assembly 150 and source assembly 180 such that probe assembly 150 is configured to detect NIR light transmitted through the biological tissue (trans-illumination mode). To provide yet another example, probe assembly 150 may be configured to detect NIR light reflected off of the biological tissue (reflectance mode) which is similar to the mode illustrated in FIG. 1.

Furthermore, various embodiments include one or more of probe assembly 150 and/or source assembly 180 facilitating imaging modes of operation including contact (probe assembly 150 and/or source assembly 180 contacting the tissue sample) or non-contact (probe assembly 150 and/or source assembly 180 not in contact with the tissue sample).

Controller assembly 160 may include processor 162 and source driver 164. Controller assembly 160 may be configured to communicate with and/or control other portions of probe assembly 150 such as detector assembly 170, for example, as will be further discussed in detail below. Additionally or alternatively, controller assembly 160 may be configured to communicate with and/or to control module 102 and/or source assembly 180 to facilitate tissue imaging.

For example, processor 162 may facilitate communications between probe assembly 150 and control module 102 via a wired or wireless connection, which may occur in accordance with any suitable type and number of communication protocols, such as a Universal Serial Bus (USB) communication protocol, for example. Processor 162 may process one or more optical signals received via detector 172, for example, convert these optical signals to digitized electrical representations thereof, and communicate these digital signals to control module 102 as NIR intensity signal data.

Processor 162 may work in conjunction with source driver 164 to cause source driver 164 to send one or more trigger signals to source assembly 180. Upon receiving these trigger signals, source assembly may emit NIR light having any suitable number of wavelengths in accordance with any suitable duration, schedule, or intensity as specified by source driver 164. For example, if source assembly 180 implements multiple NIR light sources, processor 162 may cause source driver 164 to turn on a first NIR light source corresponding to a first wavelength for a first time period, followed by a second NIR light source corresponding to a second wavelength being turned on continuously. To provide another example, processor 162 may cause source driver 164 to turn on a first and a second NIR light source simultaneously.

To provide yet another example, processor 162 may cause source driver 164 to turn on two different wavelength NIR light sources in an alternatively time-division multiplexed 'ON-OFF-ON' frequency (e.g., 10-20 Hz) to dynamically image the near-infrared signals at any suitable number of wavelengths (e.g., two). These embodiments may be particularly useful for real-time imaging and extracting the data for further processing to obtain oxy- and deoxy-hemoglobin changes in real-time (as will be described later).

Detector assembly 170 may be implemented with any suitable number and/or type of detectors to facilitate the detection of NIR light attenuated through, transmitted through, and/or reflected off the tissue sample. For example, detector assembly may include a detector 172, one or more optical filters 174, and one or more optical lenses 176.

Detector 172 may be implemented as any suitable type of device to measure NIR light attenuated through, transmitted through, and/or reflected off the tissue sample by the tissue sample as one or more optical signals, which may be converted into electrical signals and digitized via one or more of detector 172 or processor 162. For example, detector 172 may be implemented as a photomultiplier tube (PMT), a charge-coupled device (CCD), an intensified CCD (ICCD), an avalanche photodiode (APD), a complementary metal oxide semiconductor (CMOS) camera device, etc. A CCD-based or CMOS-based detector may be especially advantageous when a larger area of a tissue sample is to be imaged.

In an embodiment, processor 162 may synchronize detection of NIR light by detector 172 with source driver 164 triggering illumination from source assembly 180. In this way, detector 172 may detect NIR light attenuated through, transmitted through, and/or reflected by the tissue sample each time the tissue sample is illuminated by NIR light via source assembly 180.

One or more optical lenses 176 may be configured to focus the received NIR light and to pass the focused NIR light through one or more optical filters 174. Optical filters 174 may be configured as any suitable type of one or more optical filters (e.g., single or two or more optical filters working in conjunction with one another) to pass the received NIR signal to detector 172 so that the NIR light may be sampled, measured, and converted to one or more optical signals.

For example, in applications utilizing fluorescence imaging, a contrast agent may be injected into the tissues sample. In such an application, the fluorescence signal may be measured along with the NIR signal attenuated through, transmitted through, and/or reflected from the tissue surface. In addition, one or more optical filters 174 may be used to acquire one or both the fluorescence (or emission) and NIR signal received by detector 172.

Tracking target 165 may be affixed to or otherwise disposed on probe assembly 150 and configured to provide positional data indicative of the motion of probe assembly 150. As will be further discussed below, this data positional data may be used to facilitate co-registration of acquired images of the subject tissue by control module 102. In an embodiment, tracking target 165 may be configured as any suitable type of motion tracking device, such as a light-based tracking device, an electromagnetic tracking device, an ultrasonic tracking device, etc. In this way, tracking target 165 may track the position of probe assembly 150 (or the relative positions of the probe assembly 150 and the subject tissue, since the position of the subject tissue being imaged may be known or acquired using any suitable techniques or other tracking targets) while the tissue sample is being imaged. This positional data may include any suitable number of dimensions, such as two-dimensional or three-dimensional positional information, for example, based upon the desired imaging application, sensitivity, etc.

Control module 102 may be configured to measure, receive, and/or monitor one or more data signals associated with the tissue imaging performed by probe assembly 150 in conjunction with source assembly 180. Control module 102 may include a central processing unit (CPU) 104, a graphics processing unit (GPU) 106, a display 108, a communication unit 110, a user interface 112, and a memory 114. In some embodiments, control module 102 may be implemented as any suitable computing device separate from probe assembly 150, such as a laptop computer, a dedicated imaging control system, a personal computer, a tablet computer, etc. In other embodiments, one or more portions of control module 102 (or control module 102 in its entirety) may be implemented as part of probe assembly 150, such as a subsystem of probe assembly 150, a modular device affixed to probe assembly 150, etc.

Display 108 may be implemented as any suitable type of display and may facilitate user interaction in conjunction with user interface 112, such as a laptop display, a tablet computer display, a capacitive touch screen display, a resistive touch screen display, etc. In various aspects, display 108 may be configured to work in conjunction with processor 104 and/or GPU 106 to display one or more NIR images once NIR signal data is received by communication unit 110 and/or processed by processor 104 executing instructions in one or more modules stored in memory 114, which is further discussed below.

Communication unit 110 may be configured to process, send data to, and/or receive data from probe assembly 150 and/or source assembly 180. Communication unit 110 may be configured to communicate with probe assembly 150 and/or source assembly 180 in accordance with any suitable type and/or number of wired and/or wireless communication protocols (e.g., a Universal Serial Bus (USB) protocol). For example, communication unit 110 may receive NIR signal data from probe assembly 150 for analysis, processing, and image mapping. To provide another example, communication unit 110 may receive light source information, time series data, frequency multiplexing data, system data (e.g., quantum efficiency data) from source assembly 180 and/or from probe assembly 150 that may be used to facilitate the hemodynamic imaging and/or post-process operations.

User interface 112 may be configured to receive user-input and to facilitate user interaction with control module 102. For example, user-interface 112 may be implemented as a "soft" keyboard that is displayed on display 108, an external hardware keyboard communicating via a wired or a wireless connection (e.g., a Bluetooth keyboard), an external mouse, or any other suitable user-input device.

User-interface 112 may include a microphone configured to receive user input in the form of voice input, such as voice commands, for example. In some aspects, voice commands received via user interface 112 may be converted to text, for example, via processor 104. In this way, user interface device 112 may allow a user to enter text in lieu of typing. User interface 112 may facilitate a user adjusting, modifying, changing, etc., one or more options or settings of control module 102 depending on a particular implementation. For example, a user may utilize user interface 112 to change display settings, to change an NIR imaging mode (e.g., static versus real-time) to manually select a region of interest (ROI), to select a type of analysis (e.g., subtraction, frequency, spatio-temporal, etc.) used in the imaging process as further discussed below, etc.

Processor 104 and/or GPU 106 may be configured to communicate with memory 114 to store to and read data from memory 114 and to process data received via probe assembly 150. In various embodiments, processor 104 and/or GPU 106 may be implemented as any suitable type of generic or application-specific processor. For example, processor 104 may be implemented as a digital signal processor (DSP) configured to perform one or more signal processing operations on one the NIR data received from probe assembly 150 to facilitate one or more functions of the embodiments as described herein.

In accordance with various embodiments, memory 114 is a computer-readable non-transitory storage device that may include any combination of volatile (e.g., a random access memory (RAM), or a non-volatile memory (e.g., battery-backed RAM, FLASH, etc.). Memory 114 may be configured to store instructions executable on processor 104 and/or GPU 106. These instructions may include machine-readable instructions that, when executed by CPU 102 and/or GPU 106, cause CPU 102 and/or GPU 106 to perform various acts.

In accordance with various embodiments, processor 104 and/or GPU 106 may store data in any suitable portion of memory 114. This data may include, for example, data received via communication unit 110 from probe assembly 150 and/or source assembly 180, such as NIR signal data, light source information, time series data, frequency multiplexing data, system data, etc. In accordance with such embodiments, processor 104 and/or GPU 106 may be configured to read data from memory 114 to perform the various hemodynamic imaging and/or post-processing operations as described herein.

Tracking module 115, image processing/storage module 116, image alignment/ROI selection module 118, co-registration module 119, efficiency compensation module 120, analysis module 122, and hemodynamic concentration calculation module 130 are portions of memory 114 configured to store instructions executable by processor 104 and/or GPU 106. Analysis module 122 is a portion of memory 114 on which one or more of subtraction analysis module 124, frequency analysis module 126, and/or spatio/temporal analysis module 128 operates.

In accordance with various embodiments, any of tracking module 115, image processing/storage module 116, image alignment/ROI selection module 118, co-registration module 119, efficiency compensation module 120, analysis module 122, and/or hemodynamic concentration calculation module 130 may operate as a separately executable software application, a plugin that extends the functionality of another software application such as a web browser, an application programming interface (API) invokable by a software application, etc.

The instructions included within any of image processing/storage module 116, image alignment/ROI selection module 118, co-registration module 119, efficiency compensation module 120, analysis module 122, and/or hemodynamic concentration calculation module 130 may be compiled and executable on processor 104 and/or GPU 106 directly, or not compiled and interpreted by the processor 104 and/or GPU 106 on a runtime basis.

Tracking module 115 may include instructions that, when executed by processor 104 and/or GPU 106, causes processor 104 and/or GPU 106 to facilitate processor 104 to receive and/or process positional data from tracking target 165. For example, tracking module 115 may include instructions that, when executed by processor 104 and/or GPU 106, causes processor 104 to receive positional data from tracking target 165 via communication unit 110/or GPU 106 to track the movement of probe assembly 150. This positional data may be received with the NIR intensity signal data received via communication unit 110. In this way, the position of probe assembly 150 (or the relative positions of the probe assembly 150 and the subject tissue) may be determined while the tissue sample is being imaged for each sample. This positional data may be stored in any suitable portion of memory 114 and later accessed, for example, in accordance with any of the co-registration techniques and/or post-processing analyses further discussed herein.

Image processing/storage module 116 may include instructions that, when executed by processor 104 and/or GPU 106, causes processor 104 and/or GPU 106 to receive, store, and/or process data received from probe assembly 150 via communication unit 110. In various embodiments, this data may include, for example, NIR intensity signal data received via communication unit 110. In various embodiments, the NIR intensity signal data may be received, stored, and processed in accordance with a selected analysis (e.g., subtraction, frequency, spatio-temporal, etc.) to view the plotted data (e.g., as a static image or in real time as the image is scanned) by probe assembly 150.

In various embodiments, the NIR intensity signal data may be processed in accordance with one or more post-processing analyses to yield various types of data and/or images. That is, the changes in NIR intensity signal data over an imaged region may be used to display a graphical representation of mapped NIR intensity of an imaged tissue. In some embodiments, the NIR intensity signal data is first processed to yield hemodynamic data (e.g., changes in HbO concentrations, HbR concentrations, HbT concentrations, water concentrations, etc.) which in turn may be processed in accordance with one or more post-processing operations (e.g., subtraction and masking, frequency analysis, spatio-temporal analysis, etc.).

In other embodiments, however, the NIR intensity signal data may be processed in accordance with one or more post-processing analyses to yield various types of data without first converting the NIR intensity signal data to hemodynamic data. As will be further discussed below, first converting the NIR intensity signal data to hemodynamic data may provide additional details once the post-processing operations are performed on the hemodynamic data (e.g., viewing pulse information separately for changes in HbO and HbR concentrations in an imaged tissue, viewing spatial and temporal changes in HbO, HbR, and/or HbT hemoglobin concentrations, etc.).

Regardless of whether the NIR intensity signal data is first converted to hemodynamic data or the type of post-processing analysis that is implemented, embodiments include the NIR intensity signal data first being prepared in accordance with one or more pre-processing techniques. Pre-processing techniques may include, for example, storing the NIR intensity signal data, performing image alignment on the NIR intensity signal data, selecting a ROI from one or more of the NIR image samples, etc. As will be discussed further below, image processing/storage module 116 and/or image alignment/ROI selection module 118 may, when executed by processor 104 and/or GPU 106, facilitate such pre-processing functionality.

Image processing/storage module 116 may include instructions that, when executed by processor 104 and/or GPU 106, causes processor 104 and/or GPU 106 to store the NIR intensity signal data for one or more tissues samples as image frames in accordance with any suitable sampling rate (e.g., 1 Hz, 10 Hz, 20 Hz, etc.) on a per-wavelength basis. For example, if source assembly 180 implements two different wavelength NIR light sources for tissue imaging, communication unit 110 may receive the NIR intensity signal data for each wavelength NIR light source based upon the time-division multiplexing illumination schedule set by probe assembly 150.

As the tissue is imaged over a period of time, one or more NIR intensity image samples may be generated based upon the sampling rate. Processor 104 and/or GPU 106 may execute instructions stored in image processing/storage module 116 to separately store the one or more NIR intensity image samples for each wavelength. In this way, the separated NIR intensity image samples may represent each frame of a video of the imaged tissue sample for each NIR wavelength. The one or more NIR intensity image samples may be stored in any suitable portion of memory utilized by or associated with control module 102, such as memory 114, for example.

Image alignment/ROI selection module 118 may include instructions that, when executed by processor 104 and/or GPU 106, causes processor 104 and/or GPU 106 to perform image alignment and/or ROI selection from the one or more NIR intensity image samples. Image alignment may be utilized to re-align the NIR intensity image samples and/or to reduce motion artifacts caused by a misalignment of the NIR intensity image samples of the same imaged tissue region over a period of time.

In an embodiment, one or more portions of the one or more NIR intensity image samples (or the entire NIR intensity image samples) may be selected for each NIR wavelength. In some embodiments, this process may be manually performed by a user operating control module 102 via user interface 112, for example. In accordance with such embodiments, a user may compare several aligned NIR intensity image samples, perform masking or cropping of common areas, etc., to select a ROI for additional processing of the NIR intensity signal data as further discussed below.

In other embodiments, however, the image alignment process may be performed automatically by processor 104 and/or GPU 106 executing instructions stored in image alignment/ROI selection module 118. In accordance with such embodiments, image alignment/ROI selection module 118 may include instructions facilitating any suitable algorithm that may be executed to perform ROI selection using any suitable technique. For example, feature-based registration may be performed using one of the NIR intensity image samples as a reference image (e.g., the first one received for each NIR wavelength) to establish a correspondence between a number of distinct points among each of the NIR intensity image samples.

To provide another example, any suitable transformation algorithm may be utilized to facilitate the image alignment process, such as linear transformations, rotation transformations, scaling transformations, translation transformations, Affine transforms, radial basis functions (e.g., thin-plate or surface splines, multiquadrics, compactly-supported transformations, etc.), physical continuum models, large deformation models (diffeomorphisms), etc. Image alignment may be utilized to re-align the NIR intensity image samples and/or to reduce motion artifacts caused by a misalignment of the NIR intensity image samples of the same imaged tissue region over a period of time.

Co-registration module 119 may include instructions that, when executed by processor 104 and/or GPU 106, causes processor 104 and/or GPU 106 to co-registration of one or more NIR intensity image samples with an image of the tissue sample. In accordance with such embodiments, processor 104 and/or GPU 106 may register, or correlate, the NIR intensity image sample data (or converted hemodynamic data) onto a two or three-dimensional image of a portion of the imaged tissue region (or the entire imaged tissue region). This may be implemented using, for example, the positional information of probe assembly 150 received and/or processed via tracking module 115. In this way, the positional data correlates a position in space over the imaged tissue region to a location in which the image was acquired. For example, one or more NIR intensity image samples may be overlaid, or co-registered, with an image of the tissue sample (e.g., a picture or non-NIR image) such that a coordinate location of the portion being viewed (e.g., a selected ROI) within a tissue image may be appropriately identified.

In this way, co-registration of NIR intensity image samples allow a user to navigate an imaged biological tissue such that positional data is relayed to the user. This may be particularly useful, for example, if a tumor is found within a biological tissue sample, as the co-registration process allows a user to locate the position of the ROI corresponding to the tumor within the biological tissue sample.

Efficiency compensation module 120 may include instructions that, when executed by processor 104 and/or GPU 106, causes processor 104 and/or GPU 106 to compensate for differences in the quantum efficiency of detector 172 at different wavelengths. In an embodiment, efficiency compensation module 120 may include instructions that, when executed by processor 104 and/or GPU 106, causes processor 104 and/or GPU 106 to further process aligned NIR intensity image samples by compensating for differences in the quantum efficiency of detector 172 at different wavelengths.

For example, if detector 172 is implemented as a CCD or CMOS detector, then the CCD or CMOS efficiency, respectively, for each wavelength may be applied to the NIR intensity image sample data for each wavelength to compensate for differences between NIR intensity image samples measured at different NIR wavelengths. By compensating for the different quantum efficiency at each NIR wavelength, the NIR intensity image samples may be subsequently analyzed and mapped appropriately without introducing errors otherwise caused by these differences. In single wavelength imaging embodiments, such compensation may be unnecessary, and efficiency compensation module 120 may be omitted in accordance with such embodiments.

Furthermore, upon processing the NIR intensity image samples to account for the efficiency of detector 172, embodiments optionally include image alignment/ROI selection module 118 having instructions that, when executed by processor 104 and/or GPU 106, causes processor 104 and/or GPU 106 to further process the NIR intensity image samples by determining a region-of-interest (ROI) within the (now aligned and compensated) NIR intensity image samples.

In various embodiments, image alignment/ROI selection module 118 may include instructions for one or more different functions that may vary based upon a particular implementation of system 100. For example, alignment of NIR intensity image samples may be performed for NIR images obtained at single or multiple NIR wavelengths, while feature-based registration techniques may be used for multiple NIR wavelength implementations.

In various embodiments, this processing may include manual selection by a user operating control module 102 via user interface 112, for example, to crop or otherwise select the ROI. In other embodiments, the selection of the ROI may be performed automatically, for example, using any suitable image recognition techniques to identify the ROI from characteristics of the aligned NIR intensity image samples. Regardless of how the ROI is selected, the selected ROI may be extracted from the NIR intensity image samples as a new image and the NIR intensity image constituting this new image may be used for hemodynamic data conversion and/or additional post-processing analyses.

In addition, the NIR intensity images may have noisy regions and/or regions of non-interest. Such regions may also have excess light leakage that reduces the contrast in the ROIs. As a result, image alignment/ROI selection module 118 may optionally include instructions that, when executed by processor 104 and/or GPU 106, causes processor 104 and/or GPU 106 to mask areas outside of the ROI to improve the image contrast, which is further discussed below with reference to FIGS. 3A-B.

Once the NIR intensity image samples are collected, stored by respective wavelength, aligned, adjusted for image capture unit efficiency, filtered, and/or the ROI set, control module 102 may provide additional analytical options regarding how the NIR intensity image samples are further processed and displayed.

In an embodiment, subtraction analysis module 124 may include instructions that, when executed by processor 104 and/or GPU 106, causes processor 104 and/or GPU 106 to perform subtraction of aligned NIR intensity images from the reference image for each respective wavelength. Additionally or alternatively, subtraction analysis module 124 may include instructions that, when executed by processor 104 and/or GPU 106, causes processor 104 and/or GPU 106 to mask the resulting image to remove unwanted regions around the ROI, to remove noise introduced by these portions of the resulting images, and/or to improve contrast.

For example, a subtraction analysis may be implemented to subtract each NIR intensity image sample sequentially from the reference sample to generate one or more resulting "difference" NIR intensity images representing a difference between each NIR intensity image sample and the reference NIR intensity sample from which it was subtracted. If one or more alignment techniques are used, embodiments optionally include the subtraction analysis being performed on the aligned NIR intensity image samples. These difference NIR intensity image samples may also be optionally masked and viewed successively to provide a real time view of the imaged tissue. To provide another example, the subtraction analysis may be performed on two static NIR intensity images obtained from the same or different tissue region instead of being viewed in real-time.

In an embodiment, frequency analysis module 126 may include instructions that, when executed by processor 104 and/or GPU 106, causes processor 104 and/or GPU 106 to extract frequency components from the NIR intensity images at one or more points in the imaging surface. For example, the NIR intensity over successive NIR image samples change over time as a result of changes in blood flow at various points within the tissue sample. By extracting the frequency components from the NIR intensity signal data, a determination may be made regarding the pulse (i.e., hemodynamic response) at one or more points within an NIR intensity image and how the pulse changes in real time. In this way, frequency analysis module 126 may include instructions to facilitate displaying a hemodynamic response activity map by showing hemodynamic response mapped onto one or more point within an NIR intensity image.

Additionally or alternatively, frequency analysis module 126 may include instructions that, when executed by processor 104 and/or GPU 106, causes processor 104 and/or GPU 106 to perform one or more frequency analyses on the NIR intensity signal data before or after the NIR intensity signal data has been converted to hemodynamic data. When frequency analysis is performed on the NIR intensity signal data that has already been converted to hemodynamic data, frequency analysis module 126 may advantageously facilitate the determination of frequency response information of different components of the hemodynamic data.

For example, if frequency analysis is performed on the NIR intensity signal data before being converted to hemodynamic data, then the frequency analysis may provide information regarding the frequency components of the NIR intensity signal data as a whole. On the other hand, if frequency analysis is performed on the NIR intensity signal data after being converted to hemodynamic data, then the frequency analysis may provide information regarding the frequency components of the changes in HbO, HbR, and/or HbT hemoglobin concentrations within an imaged tissue sample. That is, once converted to hemodynamic data, the hemodynamic data may be used as the source data for one or more post-processing analyses (in this case frequency analysis, but other post-processing analyses may use the hemodynamic data as well, which is further discussed below). In the case of frequency analysis, this may advantageously provide pulse information, for example, for the change in each hemoglobin concentration level.

In various embodiments, frequency extraction may be performed using any suitable frequency transform techniques, such as a Fourier Transform, for example. In accordance with such embodiments, instructions stored in frequency analysis module 126 may cause processor 104 and/or GPU 106 to perform Fourier Transform calculations on the NIR intensity signal data from one or more NIR intensity image samples.

In other words, the NIR intensity signal data at a particular point within each of the NIR intensity image samples may represent an NIR intensity signal. Over several NIR intensity image samples, the NIR intensity signal data at this point varies over a time in accordance with the successive NIR image samples. A Fourier Transform may be calculated from this time-varying NIR intensity signal data to generate frequency components that may be mapped to each NIR intensity image sample using any suitable scaling and display technique to indicate changes in the power of the frequency components in real-time. The changes in the power of the mapped frequency components at one or more points within the NIR intensity image samples may then be utilized to determine any suitable type of information based upon the different frequency components power levels (e.g., pulse information) at each of the corresponding points in the imaged tissue sample.

In an embodiment, spatio-temporal analysis module 128 may include instructions that, when executed by processor 104 and/or GPU 106, causes processor 104 and/or GPU 106 to extract one or more spatio-temporal features from the NIR intensity images.

In various embodiments, spatio-temporal features may be extracted from the NIR intensity signal data using any suitable techniques to extract relevant details represented by the NIR intensity image data by reducing the dimension of the data. For example, using a sampling rate of 5 Hz, a tissue imaged for 30 seconds will result in 150 NIR intensity image samples. If each NIR intensity image sample has a size of 150×150 pixels, a large number of data samples (over three million points) may be stored representing the NIR intensity signal data at each pixel across each of the 150 NIR intensity image samples. Therefore, to efficiently extract one or more spatio-temporal features from the NIR intensity images, instructions included in spatio-temporal analysis module 128, when executed by processor 104 and/or GPU 106, may cause processor 104 and/or GPU 106 to reduce this data set by applying a suitable factorization, matrix decomposition, transformation, etc., to the set of NIR intensity signal data represented by the NIR intensity image samples for each NIR wavelength.

For example, instructions stored in spatio-temporal analysis module 128 may cause processor 104 and/or GPU 106 to calculate singular value decomposition (SVD), principal component analysis (PCA), and/or independent component analyses (ICA), etc., of a selected ROI within an NIR intensity image sample or an entire imaged region of the NIR intensity image sample.

To provide an illustrative example, a series of NIR intensity image samples may include an aggregation of several anatomical features in the imaged tissue that may represent different blood circulatory responses. Examples of these various anatomical features may include the tissue surface, arteries, veins, capillaries, etc. By applying a suitable reconstruction or decomposition technique (e.g., SVD, PCA, ICA, etc.) dominant eigenvalue signal components may be extracted from the NIR intensity image sample data based upon the NIR data at a single point in time (sampling point).

Each of the dominant eigenvalue signal components may be mapped using any suitable scaling and display technique to generate reconstructed images corresponding to each spatio-temporal feature. These dominant eigenvalue signal components may be mapped in a static or dynamic nature. When mapping one or more of the dominant eigenvalue signal components as a static image sample, different tissue types may be displayed that correspond to their respective dominant eigenvalue signal components at a single sampling point. Thus, the process of selecting and viewing different eigenvalue signal components from an NIR intensity image sample may function as a filter to differentiate between different types of tissues present in the imaged tissue.

Once extracted from the NIR intensity image sample data (in real time), the one or more signal components likewise vary in time over each of the tissue image samples. As a result, the dominant eigenvalues extracted from the NIR intensity image sample data for each signal component represent a time series. Mapping and displaying the time series corresponding to each of the dominant eigenvalues allows for a graphical representation to be viewed representing changes in time for the one or more signal components. Examples of these graphical representations may include videos, line plots, a profile of a single point or selected ROI over time, etc.

In this way, by extracting dominant eigenvalue signal components from a set of NIR intensity image samples, different types of tissues within a tissue sample may be visualized as well as temporal changes in each of the different types of tissues over time caused by, for example, changes in blood flow.

Additionally or alternatively, the NIR intensity signals may be processed using any suitable mathematical models, which will be discussed in more detail below, to extract the changes in oxy- (HbO), deoxy-hemoglobin (HbR), and total hemoglobin (HbT) concentrations as relative changes. In various embodiments, these HbO, HbR, and HbT values may be obtained as static or dynamic data signals in real-time. The data may be then be analyzed in terms of the real-time changes in HbO, HbR, and HbT data signals over time at any given point in the imaged region, over the selected ROI in the imaged region, or over the entire imaged region. The time-dependent HbO and/or HbR signal data may represent waveforms, for example. Performing frequency analysis on one or more of these waveforms, as previously discussed, may also yield the rate of blood flow (pulse rate).

In an embodiment, the changes in HbO and HbR concentrations may be derived from the NIR intensity signals by calculating an optical density of the imaged tissue sample and using this information to calculate the hemodynamic concentrations.

In an embodiment, hemodynamic concentration calculation module 130 may include instructions that, when executed by processor 104 and/or GPU 106, causes processor 104 and/or GPU 106 to calculate one or more tissue features from the imaged tissue using the NIR intensity signals. Examples of the one or more tissue features that may be determined from the NIR intensity signals may include, for example, changes in water concentration, changes in HbO concentration, changes in HbR concentration, changes in HbT concentration, etc.

To facilitate calculating the one or more tissue features, an optical density of the imaged tissue sample may be calculated using any suitable mathematical techniques, algorithms, etc. In an embodiment, hemodynamic concentration calculation module 130 may include instructions facilitating the determination of the optical density, OD, in accordance with Eqn. 1:

$$\Delta OD^\lambda = -\ln \frac{I_{Final}}{I_{Initial}} = (\varepsilon_{HbO}^\lambda \Delta[HbO] + \varepsilon_{HbO}^\lambda \Delta[HbR])B^\lambda L \quad \text{Eqn. 1}$$

In Eqn. 1 above, $\Delta OD^\lambda$ represents a change in the optical density relative to the power of the NIR light illuminating the tissue sample and how much is absorbed by the tissue sample at a particular wavelength $\lambda$. $I_{Final}$ represents the power of the NIR light that is attenuated through, transmitted through, and/or reflected by the tissue sample and detected by the detector assembly, $I_{Initial}$ represents the power of the NIR light illuminating the tissue sample, which may be determined by using the intensity at the first sampled point in the time series (of successive samples of an imaged tissue sample) as a reference, $\varepsilon_{HbO}^\lambda$ represents the extinction coefficient (at a wavelength $\lambda$) corresponding to the standard parameter for oxy-hemoglobin, $E_{HbR}^\lambda$ represents the extinction coefficient (at a wavelength $\lambda$) corresponding to the standard parameter for deoxy-hemoglobin, $\Delta[HbO]$ represents a change in oxy-hemoglobin, $\Delta[HbR]$ represents a change in deoxy-hemoglobin, $B^\lambda$ represents a factor based upon the quantum efficiency of the detector at a specific wavelength $\lambda$, and L represents the distance the NIR light traveled from the point it was launched (e.g., source assembly 180) to the point it was detected (e.g., probe assembly 150). In some embodiments, the value of L may be left unchanged for the calculation of either $\Delta[HbO]$ or $\Delta[HbR]$, and may be set to a unit value.

In an embodiment, hemodynamic concentration calculation module 130 may include instructions facilitating the determination of the change in the HbO and HbR concentrations in accordance with Eqns. 2 and 3:

$$\Delta[HbO] = \frac{\varepsilon_{HbR}^{\lambda_1} \frac{\Delta OD^{\lambda_2}}{B^{\lambda_2}} - \varepsilon_{HbR}^{\lambda_2} \frac{\Delta OD^{\lambda_1}}{B^{\lambda_1}}}{(\varepsilon_{HbR}^{\lambda_1}\varepsilon_{HbO}^{\lambda_2} - \varepsilon_{HbR}^{\lambda_2}\varepsilon_{HbO}^{\lambda_1})L} ; \text{and} \quad \text{Eqn. 2}$$

$$\Delta[HbR] = \frac{\varepsilon_{HbO}^{\lambda_2} \frac{\Delta OD^{\lambda_1}}{B^{\lambda_1}} - \varepsilon_{HbO}^{\lambda_1} \frac{\Delta OD^{\lambda_2}}{B^{\lambda_2}}}{(\varepsilon_{HbR}^{\lambda_1}\varepsilon_{HbO}^{\lambda_2} - \varepsilon_{HbR}^{\lambda_2}\varepsilon_{HbO}^{\lambda_1})L} \quad \text{Eqn. 3}$$

In Eqns. 2 and 3 above, $\lambda_1$ and $\lambda_2$ represent the two different NIR wavelengths used to obtain the changes in oxy- (HbO) and deoxy-hemoglobin concentrations (HbR) of the imaged tissue region, such as 690 nm and 830 nm, respectively, for example. Upon calculation of the changes in the HbO and HbR concentrations, this data may be summed to calculate changes in total hemoglobin concentrations (HbT). One or more of the changes in the HbO, HbR, and/or HbT concentrations may be displayed as part of the NIR intensity signal data, which may be viewed in real-time or as a static images, and/or may be viewed further processed in accordance with one or more post-processing analyses, such as subtraction analysis, frequency analysis, spatio-temporal analysis, etc., which is further discussed below.

In various embodiments, the hemodynamic conversion of the NIR intensity signal data and the one or more post-processing analyses (which may be performed on the NIR intensity signal data or the hemodynamic data converted from the NIR intensity signal data) may be performed in any suitable order. For example, a subtraction and masking analysis may first be performed followed by a frequency analysis and a spatio-temporal feature analysis. To provide another example, the frequency analysis may first be performed followed by the subtraction and masking analysis.

FIG. 2 illustrates an example graphical user interface (GUI) 200 for displaying raw and processed NIR image data in accordance with an exemplary aspect of the present disclosure. GUI 200 includes portions 202, 204, 206, and 208.

In the present embodiments, GUI 200 is an example of what may be displayed to a user on a suitable device (e.g., control module 102) to facilitate the viewing of NIR intensity images, pulse information, changes in HbO, HbR, and HbT concentrations at one or more select points on imaged regions, spatio-temporal features, etc., corresponding to an imaged tissue. Although GUI 200 illustrates several points within an imaged region, embodiments of GUI 200 may include providing information in any suitable graphical format, such as two-dimensional area plots, contour line plots, three-dimensional plots, etc.

In various embodiments, GUI 200 may be displayed using any suitable display device, such as display 108, for example, as shown in FIG. 1. GUI 200 may be implemented using any suitable format and/or design without departing from the spirit and scope of the present disclosure.

Figure 3A:
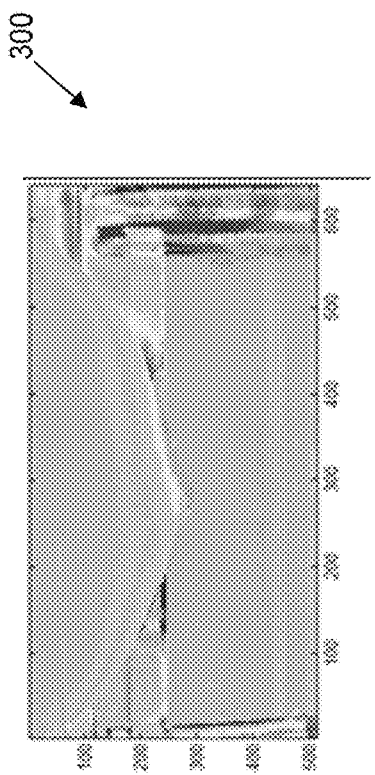
FIG. 3A illustrates an example subtracted and realigned NIR image 300 in accordance with an exemplary aspect of the present disclosure.
Figure 3B:
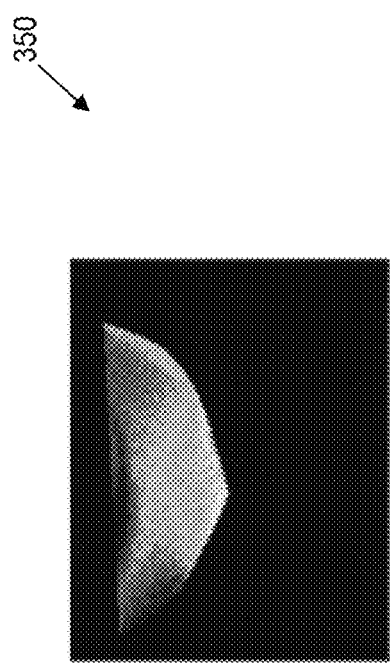
FIG. 3B illustrates an example subtracted, realigned, and masked NIR image 350 in accordance with an exemplary aspect of the present disclosure.
Figure 4:
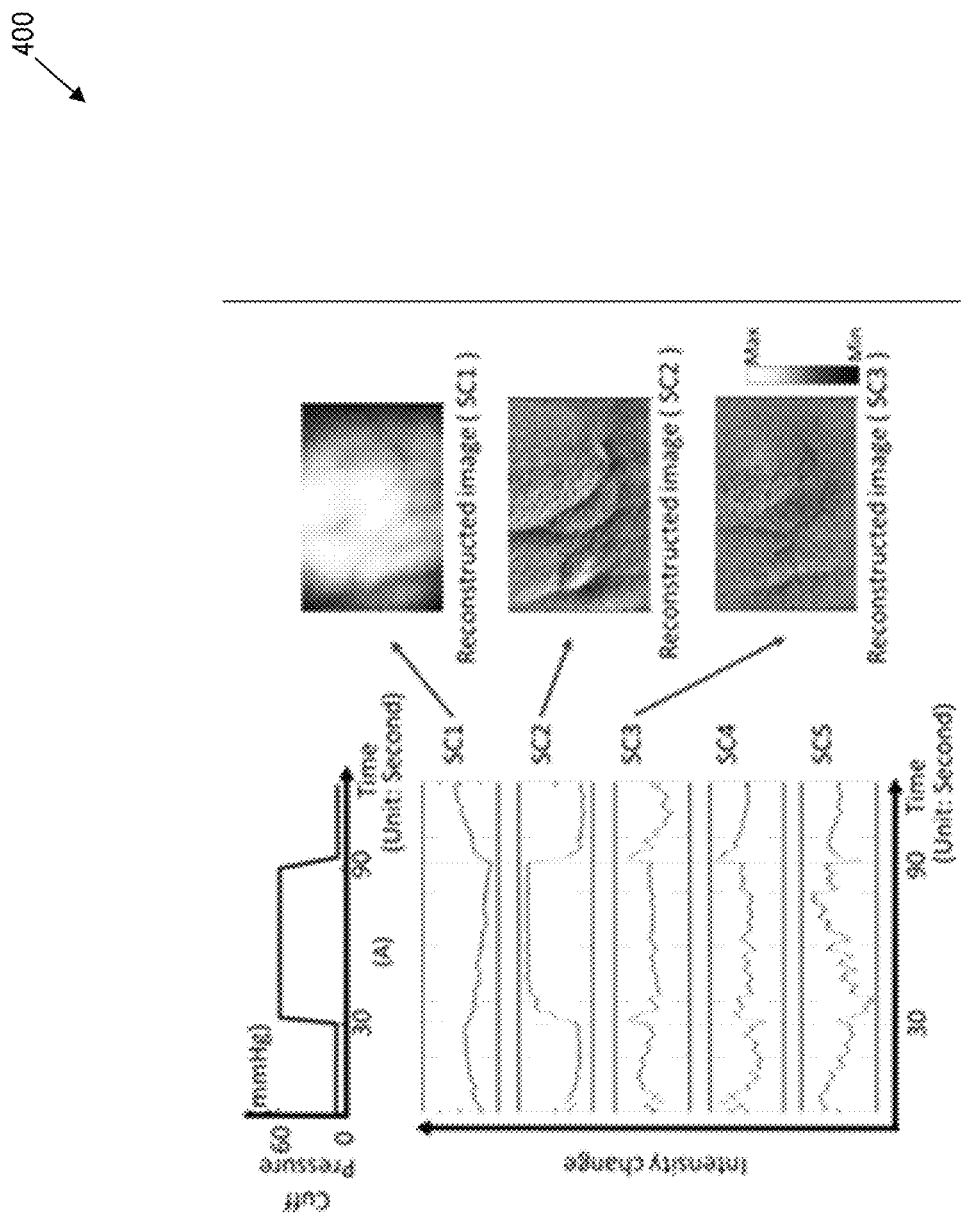
FIG. 4 illustrates exemplary signal component plots and reconstructed images 400 illustrating spatio-temporal features in accordance with an exemplary aspect of the present disclosure.

Portion 202 may include any suitable graphic, information, labels, etc., to display any suitable image in accordance with the various embodiments disclosed herein, such as an NIR intensity image (as shown in FIG. 2), a subtracted and/or masked NIR image (as shown in FIGS. 3A and 3B), spatio-temporal features (as shown in FIG. 4), pulse information, a hemodynamic map, etc. Again, the hemodynamic map data may be subjected to post-processing analyses and the resulting post-processing calculations displayed in portion 202, such a subtraction analysis, masking, frequency analysis, spatio-temporal analysis, a hemodynamic response activity map, etc.

Furthermore, embodiments include portion 202 displaying NIR intensity changes or hemodynamic data as part of a colored histogram of intensity distribution having any suitable scale to facilitate easily viewing the NIR intensity images. Portion 202 may include an equalizer facilitating the adjustment of contrast in conjunction with the histogram. Furthermore, although the NIR intensity map or hemodynamic data may be used to observe real time changes in NIR intensity for one or more NIR intensity image samples, portion 202 may display an NIR intensity map or hemodynamic data for a single time sample in a series of NIR intensity image samples, a dynamic two dimensional map over time, a two-dimensional video of the imaged region over time, etc.

Although not shown in FIG. 2 for purposes of brevity, one or more points may be selected within portion 202 for additional analysis. For example, as indicated in portion 208, portion 202 includes 4 selected points (signal_1, signal_2, signal_3, and signal_4) that have been marked and/or selected by a user. These points may be marked within portion 202 in any suitable manner, such as via a mouse, keyboard input, automatic default selections, etc.

Portion 204 may include any suitable graphic, information, labels, etc. to display the resulting analytical data from processing the NIR intensity signals or the hemodynamic data for the actively selected signal (signal_4) corresponding to a particular tissue location selected within portion 202. Again, portion 204 may include information based upon the selected portion of the image displayed in portion 202, which may include a point in the imaged region, information calculated over a selected ROI in the imaged region, or information calculated over the entire imaged region.

As shown in FIG. 2, signal_4 has been marked for active display by a user, as indicated in portion 208. Thus, the time series information shown in portion 208 reflects changes in HbO, HbR, and/or HbT concentrations for signal_4, which is calculated based upon NIR intensity image data at the selected location within portion 202 corresponding to the same location on the imaged tissue.

The time series information shown in portion 204 illustrates the changes in HbO, HbR, and/or HbT concentrations for a person induced by the application of a conventional blood pressure cuff applying a suitable pressure thereto (e.g., 240 mmHg) and then released at point 201. The pressure caused by the cuff causes venous occlusion and, as shown in portion 204, the changes in HbO, HbR, and/or HbT concentrations for signal_4 indicate increased fluctuations in these concentrations after pressure was released, which is to be expected from a return of blood flow to the imaged tissue sample.

Portion 206 may include any suitable graphic, information, labels, etc. to facilitate a user saving the NIR intensity images or hemodynamic data, saving the time series information once calculated and/or displayed in portion 204, etc.

Portion 208 may include any suitable graphic, information, labels, etc. to facilitate a user modifying one or more settings and/or options of GUI 200. For example, a user may select an NIR wavelength source when multiple NIR wavelength sources are used, toggle the application of CCD or CMOS efficiency to the measured NIR intensity signal data (or other type of spectral efficiency if CCD or CMOS imaging is not used), select the sampling rate, etc.

In addition, portion 206 allows a user to specify a pixel radius corresponding to a selected signal, such that the hemodynamic data, hemodynamic response (pulse information), etc., may be calculated based upon the NIR intensity signal data averaged over the indicated pixel region. In this way, a user may select varying granularities of points within portion 202 in which to view the hemodynamic data within an NIR image, pulse information, etc., derived from the NIR intensity signal data corresponding to that region (or the entire imaged region).

FIG. 3A illustrates an example subtracted and realigned NIR image 300 in accordance with an exemplary aspect of the present disclosure. Again, although NIR image 300 is shown as a black and white image, embodiments include image 300 being displayed as part of a colored histogram having any suitable scale to facilitate better viewing of changes in NIR intensity throughout NIR image 300. The example NIR image 300 shown in FIG. 3A corresponds to a breast tissue sample obtained in a trans-illuminated detected NIR intensity signal data.

In various embodiments, NIR image 300 may be displayed using any suitable display device, such as display 108, for example, as shown in FIG. 1. For example, NIR image 300 may be displayed as part of portion 202 of GUI 200, as shown in FIG. 2. In an embodiment, NIR image 300 may represent an NIR intensity image that has been subtracted and aligned by processor 104 and/or GPU 106 executing instructions stored in subtraction analysis module 124. The resulting NIR image 300, therefore, is an example of a series of NIR intensity image samples for a particular NIR wavelength being aligned and the aligned image being subtracted from a reference NIR intensity image, as previously discussed with reference to FIG. 1 for subtraction analysis. In other words, NIR image 300 may represent NIR intensity signal data that has been subjected to a subtraction post-processing analysis. Again, the subtraction post-processing analysis may be performed on the NIR intensity signal data or on NIR intensity signal data that has been converted to hemodynamic data.

FIG. 3B illustrates an example subtracted, realigned, and masked NIR image 350 in accordance with an exemplary aspect of the present disclosure. NIR image 350 may correspond to NIR image 300 being masked by processor 104 and/or GPU 106 executing instructions stored in subtraction analysis module 124 to remove unwanted regions of NIR image 300 outside of the ROI (the breast tissue in this example) and to improve the image contrast in the resulting NIR image 350.

FIG. 4 illustrates exemplary signal component plots and reconstructed images 400 illustrating spatio-temporal features in accordance with an exemplary aspect of the present disclosure. The example exemplary signal component plots and reconstructed images 400 shown in FIG. 4 correspond to a dorsum of a human hand. Although the reconstructed images are shown in FIG. 4 as black and white images, embodiments include the reconstructed images being displayed as part of a colored "heat map" having any suitable color scale corresponding to various NIR intensities to facilitate better viewing of changes in NIR intensity throughout the reconstructed images. In various embodiments, the reconstructed images may be displayed using any suitable display device, such as display 108, for example, as shown in FIG. 1. For example, the reconstructed images may be displayed as part of portion 202 of GUI 200, as shown in FIG. 2.

In the example shown in FIG. 4, the signal components correspond to changes in NIR intensity induced by the application of a conventional blood pressure cuff having pressure increased to 60 mmHg and then released, as indicated in the cuff pressure versus time graph in FIG. 4. In an embodiment, the signal components shown in FIG. 4 (SC1-SC5) may represent signal components that have been extracted from data constituting the one or more NIR image samples (or hemodynamic data converted from the one or more NIR image samples) over a sampling period (e.g., 60 seconds, 120 seconds, etc.) by processor 104 and/or GPU 106 executing instructions stored in spatio-temporal analysis module 128, as previously discussed with reference to FIG. 1.

Again, by applying a suitable reconstruction or decomposition technique (e.g., SVD, PCA, ICA, etc.) several eigenvalue signal components SC1-SC5 (or additional eigenvalue signal components as needed) may be extracted from the NIR intensity image sample data, as shown in FIG. 4. However, the primary eigenvalue signal components may be identified as SC1-SC2. As shown in FIG. 4, a comparison between the signal components indicates that the differences between SC3, SC4, and SC5 become minimal. Although FIG. 4 illustrates some differences between the SC3, SC4, and SC5 signal component line plots, the spatial mapping of SC3, SC4, and SC5 reveal minimal differences between these signal components compared to SC1 and SC2. The spatial mapping of these signal components is not shown in FIG. 4 for purposes of brevity.

As a result, mapping reconstructed images from SC3, SC4, and SC5 may not be particularly useful to identify additional features that those generated from reconstructed images of SC1 and SC2 based upon the example shown in FIG. 4. Therefore, although any of the signal components SC1-SC5 may be used to generate reconstructed images, in an embodiment, the primary eigenvalue signal components (e.g., each of SC1 and SC2 in this example) may be selected and used to generate the reconstructed images since these signal components are significantly different from one another, and are therefore indicative of the distinct spatio-temporal features of the imaged tissue sample.

The reconstructed images SC1-SC3 shown in FIG. 4 may be generated by processor 104 and/or GPU 106 executing instructions stored in spatio-temporal analysis module 128. The resulting reconstructed images shown in FIG. 4 show different anatomical patterns in each image, which correspond to the distinctive temporal maps represented by signal components SC1-SC3. In this way, the extracted spatio-temporal features may provide valuable insight by indicating various anatomical patterns within a single tissue sample from a single NIR imaging test procedure.

Figure 5:
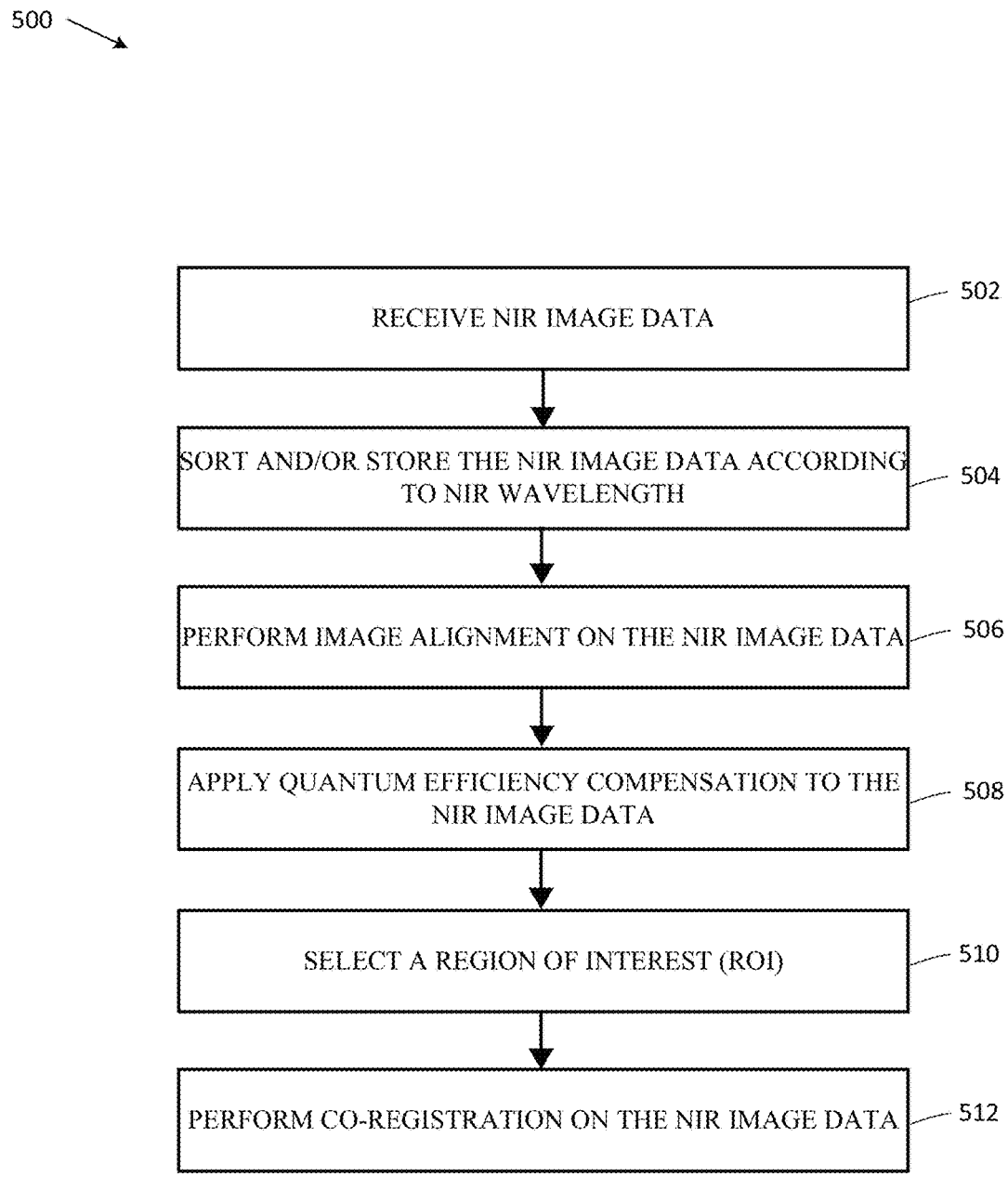
FIG. 5 illustrates an example method 500 for preparing one or more NIR images prior to further analysis in accordance with an exemplary aspect of the present disclosure.

FIG. 5 illustrates an example method 500 for preparing one or more NIR images prior to further analysis in accordance with an exemplary aspect of the present disclosure. In an embodiment, method 500 may be implemented by any suitable device, such as control module 102, for example, as shown in FIG. 1. In an embodiment, method 500 may be performed by one or more processors, modules, algorithms, applications, and/or routines, such as any suitable portion of control module 102 (e.g., processor 104) working in conjunction with one or more of image processing/storage module 116 and/or image alignment/ROI selection module 118, for example, as shown in FIG. 1.

Method 500 may start when one or more processors receive one or more NIR intensity image samples corresponding to one or more sampled tissue images (block 502) constituting video frames. This NIR image data may be received, for example, via communication unit 110 of control module 102 from probe assembly 150, as shown in FIG. 1.

Method 500 may include one or more processors sorting and/or storing the one or more NIR intensity image samples on a per-wavelength basis (block 504). These different wavelengths may correspond to, for example, the different wavelength NIR light sources used for tissue imaging by source assembly 180, as shown in FIG. 1. In an embodiment, method 500 may include identifying the one or more NIR intensity image samples based upon the time-division multiplexing illumination schedule utilized by probe assembly 150 that is synchronized with the acquisition of NIR intensity image samples by detector assembly 170 (block 504).

Method 500 may include one or more processors performing image alignment on the one or more NIR intensity image samples (block 506). In an embodiment, method 500 may include re-aligning the NIR intensity image samples using a reference NIR image to reduce motion artifacts that may be caused by a misalignment of the NIR intensity image samples (block 506).

Method 500 may include one or more processors applying quantum efficiency compensation to the one or more NIR intensity image samples (block 508). In an embodiment, method 500 may include processing the aligned NIR intensity image samples by compensating for differences in the quantum efficiency of an NIR detector (e.g., detector 172) at different wavelengths (block 508). Again, by compensating for the different quantum efficiency for each NIR wavelength, the NIR intensity image samples may be subsequently analyzed and mapped appropriately without introducing errors. Again, in some embodiments, the NIR intensity images may be sampled using a single wavelength and/or the calculation of hemodynamic data may not be performed. In accordance with such embodiments, method 500 may not include or require the application of quantum efficiency compensation to the one or more NIR intensity image samples (block 508 is omitted).

Method 500 may include one or more processors selecting a region of interest (ROI) (block 510). In an embodiment, selection of the ROI may be a manual or an automatic process (block 510). In manual ROI selection embodiments, method 500 may include a user comparing several aligned NIR intensity image samples, cropping common areas, etc., to select the ROI from the aligned NIR intensity image samples, which may then be displayed as a new image (block 510). For example, upon a user selecting a portion of an imaged tissue sample as the ROI, the selected ROI may fill the previous portion of the GUI that displayed the entire imaged tissue sample with only the selected ROI.

In automatic ROI selection embodiments, method 500 may include one or more processors using any suitable image recognition techniques, selecting the ROI in accordance with a default ROI area, etc., to identify the ROI from the NIR intensity image samples (block 510).

Method 500 may include one or more processors performing co-registration on the NIR image data (block 512). This may include, for example, one or more processors correlating registering, or correlating, the NIR intensity image sample data (or converted hemodynamic data) onto a two or three-dimensional image of a portion of the imaged tissue region (or the entire imaged tissue region) (block 512). Again, co-registration may be implemented using, for example, the positional information of probe assembly 150 received and/or processed via tracking module 115 (block 512).

Figure 6:
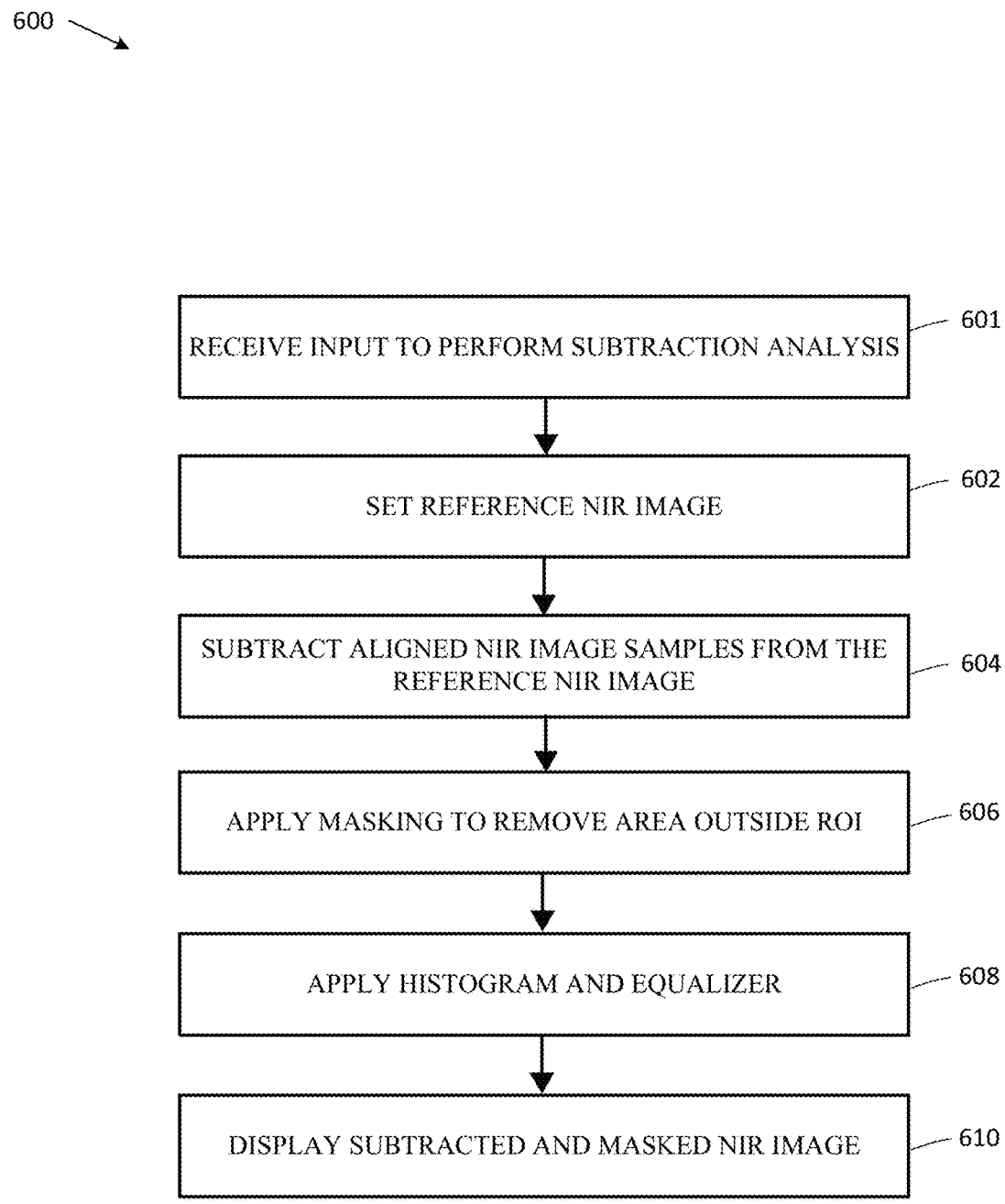
FIG. 6 illustrates an example method 600 for performing a subtraction and masking analysis in accordance with an exemplary aspect of the present disclosure.

FIG. 6 illustrates an example method 600 for performing a subtraction and masking analysis in accordance with an exemplary aspect of the present disclosure. In an embodiment, method 600 may be implemented by any suitable device, such as control module 102, for example, as shown in FIG. 1. In an embodiment, method 600 may be performed by one or more processors, modules, algorithms, applications, and/or routines, such as any suitable portion of control module 102 (e.g., processor 104) working in conjunction with subtraction analysis module 124, for example, as shown in FIG. 1. In an embodiment, method 600 may be performed, for example, on the data represented by the selected ROI from method 500 (block 510) as discussed with reference to FIG. 5.

Method 600 may start when one or more processors receives an input indicating that a subtraction analysis is to be performed on one or more NIR intensity image samples (block 601). In some embodiments, this input may be generated by a user using a suitable GUI, such as GUI 200, for example, as shown in FIG. 2 (block 601). In other embodiments, this input may be generated automatically without user intervention as the result of a set default option (block 601).

Method 600 may include one or more processors setting a reference NIR image for the subtraction analysis (block 602). This reference image may include, for example, the first NIR image received from a plurality of NIR image samples (block 602).

Method 600 may include one or more processors performing subtraction analysis by subtracting one or more NIR image samples (that may optionally be aligned) from the reference NIR image for each respective wavelength (block 604). This subtraction may include the analysis previously illustrated and discussed with reference to FIG. 3A, for example. Again, as previously discussed, if the data constituting the set of NIR intensity image samples are optionally converted to hemodynamic data, then method 600 may optionally include performing subtraction analysis on the converted hemodynamic data (block 604).

Method 600 may include one or more processors applying masking to areas outside the previously selected ROI (block 606). In an embodiment, method 600 may include masking the resulting subtracted NIR image (block 604) to remove unwanted regions around the ROI, to remove noise introduced by these portions of the resulting images, and/or to improve contrast (block 606). This masking analysis may include the masking previously illustrated and discussed with reference to FIG. 3B, for example. In some embodiments, method 600 may not include masking.

Method 600 may include one or more processors applying a histogram and/or equalizer to the subtracted and optionally masked NIR image (block 608). As previously discussed with reference to FIG. 1, method 600 may include the implementation of a colored intensity distribution heat map having any suitable scale to facilitate easily viewing the subtracted and optionally masked NIR image (block 608).

Method 600 may include one or more processors displaying the subtracted and optionally masked NIR image sample (block 610). In an embodiment, this may include displaying the resulting subtracted and optionally masked NIR image sample (blocks 604 and 606) to a suitable GUI for viewing by a user, such as displaying the masked NIR image 350 (as shown in FIG. 3B) in portion 202 of GUI 200, for example, as shown in FIG. 2 (block 610).

Figure 7:
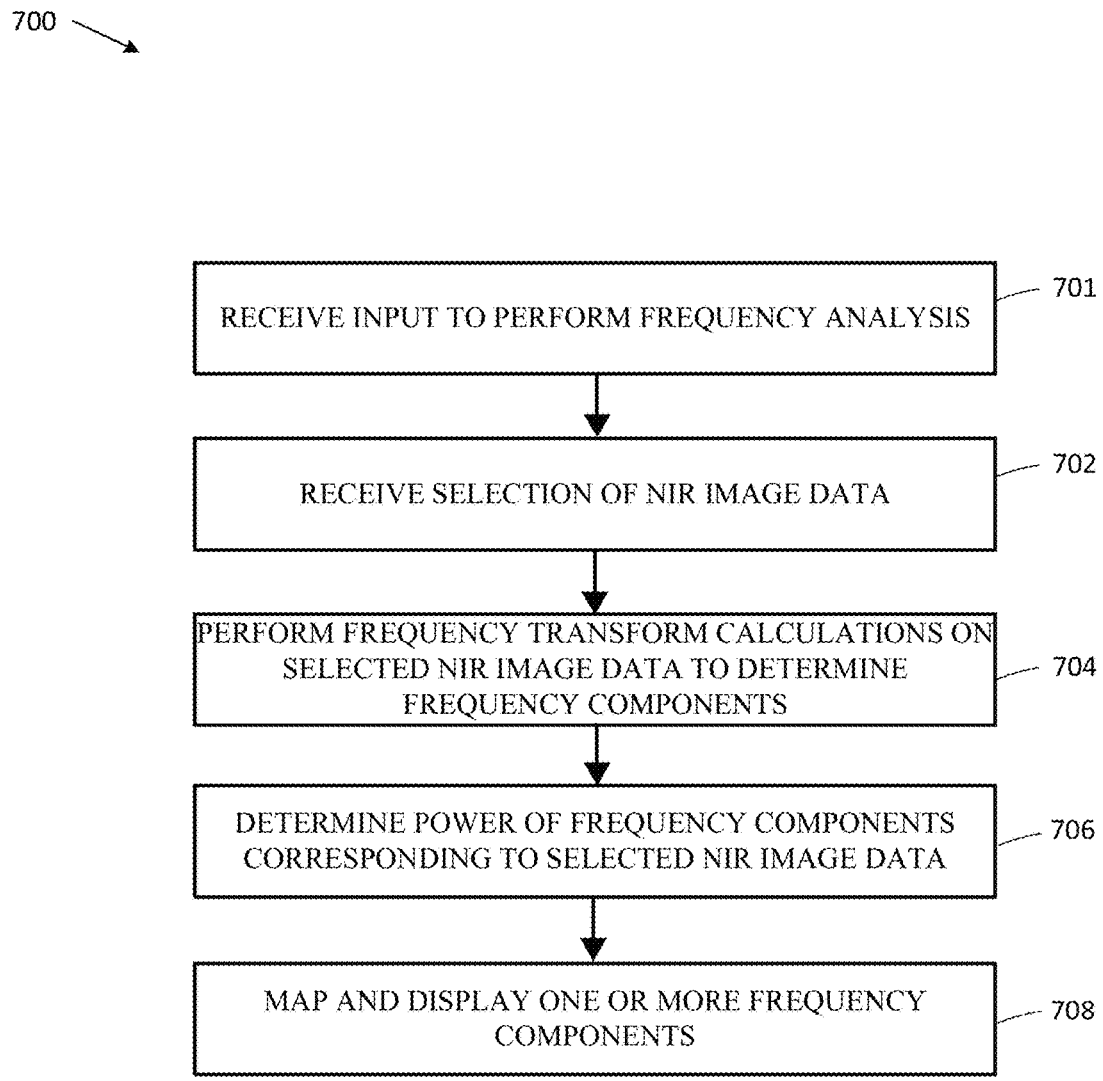
FIG. 7 illustrates an example method 700 for performing a frequency component analysis in accordance with an exemplary aspect of the present disclosure.

FIG. 7 illustrates an example method 700 in accordance with an exemplary aspect of the present disclosure. In an embodiment, method 700 may be implemented by any suitable device, such as control module 102, for example, as shown in FIG. 1. In an embodiment, method 700 may be performed by one or more processors, modules, algorithms, applications, and/or routines, such as any suitable portion of control module 102 (e.g., processor 104) working in conjunction with frequency analysis module 126, for example, as shown in FIG. 1. In an embodiment, method 700 may be performed, for example, on the data represented by the selected ROI from method 500 (block 510) as discussed with reference to FIG. 5.

Method 700 may start when one or more processors receive an input (e.g., from a user) indicating that a post-processing frequency analysis is to be performed on a set of NIR intensity image samples (block 701). In some embodiments, this input may be generated by a user using a suitable GUI, such as GUI 200, for example, as shown in FIG. 2 (block 701). In other embodiments, this input may be generated automatically without user intervention as the result of a set default option (block 701).

Method 700 may include one or more processors receiving a selection of NIR image data for frequency analysis (block 702). This may include, for example, a user specifying a point within an NIR image for which frequency analysis is to be performed (block 702). This may include an indication of a location within a displayed NIR image and/or a radius of pixels around this point for which data may be averaged when performing the frequency analysis (block 702) as previously discussed with reference to FIG. 1. This selection may also include the entire ROI (block 702).

Method 700 may include one or more processors performing a frequency transform calculation on the selected NIR image data to determine one or more frequency components (block 704). In an embodiment, this frequency transform may include a Fourier Transform (block 704) that is calculated on the selected NIR intensity signal data (block 702) constituting a data point in an NIR intensity image from a plurality of successive NIR intensity image samples (block 704). Again, as previously discussed, if the data constituting the set of NIR intensity image samples are optionally converted to hemodynamic data, then method 700 may optionally include performing frequency analysis on the converted hemodynamic data (block 704).

Method 700 may include one or more processors determining one or more frequency components of the selected NIR intensity signal data (block 706). In an embodiment, the one or more frequency components may be utilized to determine a pulse rate (block 706) at the selected point within the NIR image (block 702).

Method 700 may include one or more processors mapping and displaying the one or more frequency components (block 708). In an embodiment, this may include displaying the pulse rate for a selected area of the NIR image (block 702) within one or more portions of the GUI used to display the NIR image, such as in portion 202 of GUI 200, for example, as shown in FIG. 2 (block 708).

Figure 8:
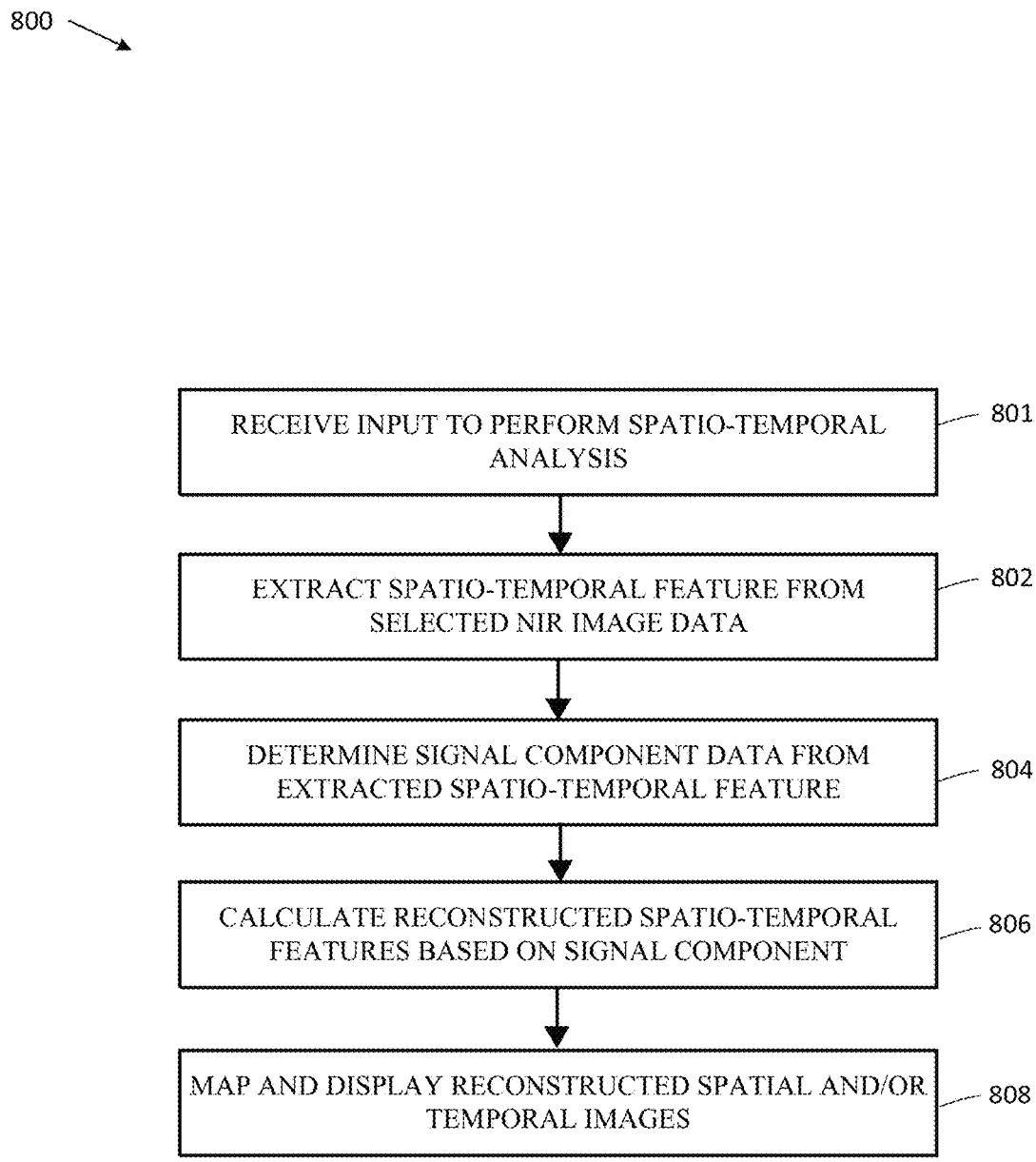
FIG. 8 illustrates an example method 800 for performing a spatio-temporal analysis in accordance with an exemplary aspect of the present disclosure.

FIG. 8 illustrates an example method 800 in accordance with an exemplary aspect of the present disclosure. In an embodiment, method 800 may be implemented by any suitable device, such as control module 102, for example, as shown in FIG. 1. In an embodiment, method 800 may be performed by one or more processors, modules, algorithms, applications, and/or routines, such as any suitable portion of control module 102 (e.g., processor 104) working in conjunction with spatio-temporal analysis module 128, for example, as shown in FIG. 1. In an embodiment, method 800 may be performed, for example, on the data represented by the selected ROI from method 500 (block 510) as discussed with reference to FIG. 5.

Method 800 may start when one or more processors receive an input (e.g., a user input) indicating that a spatio-temporal analysis is to be performed on a set of NIR intensity image samples (block 801). In some embodiments, this input may be generated by a user using a suitable GUI, such as GUI 200, for example, as shown in FIG. 2 (block 801). In other embodiments, this input may be generated automatically without user intervention as the result of a set default option (block 801).

Method 800 may include one or more processors extracting spatio-temporal features from selected NIR image data (block 802). In various embodiments, method 800 may include extracting the spatio-temporal features using any suitable techniques to reduce the dimension of the data. For example, method 800 may include reducing this data set by applying a suitable factorization, matrix decomposition, transformation, etc., to a selected set of NIR intensity signal data represented by the NIR intensity image samples for each NIR wavelength (block 802). Again, as previously discussed, if the data constituting the set of NIR intensity image samples are optionally converted to hemodynamic data, then method 800 may optionally include extracting the spatio-temporal features from the converted hemodynamic data (block 802).

Method 800 may include one or more processors determining signal component data from the one or more extracted spatio-temporal features (block 804). For example, this may include determining the dominant eigenvalue signal components from the extracted features (block 804), as previously discussed with reference to FIG. 4.

Method 800 may include one or more processors calculating reconstructed spatio-temporal features based on the signal component data (block 806). This may include, for example, a reconstructed static image sample (block 806) indicating spatial features in the tissue sample. This may also include, for example, calculating a time series from the set of dynamic image samples that indicate spatial and temporal changes in the tissue sample over one or more of the tissue image samples (block 806).

Method 800 may include one or more processors mapping and displaying the calculated reconstructed static or dynamic spatial and temporal images (block 808). In an embodiment, this may include displaying the calculated static or dynamic reconstructed temporal features (block 806) on a suitable GUI for viewing by a user, such as displaying one or more of the reconstructed images SC1-SC3 (as shown in FIG. 4) in portion 202 of GUI 200, for example, as shown in FIG. 2 (block 808).

Figure 9:
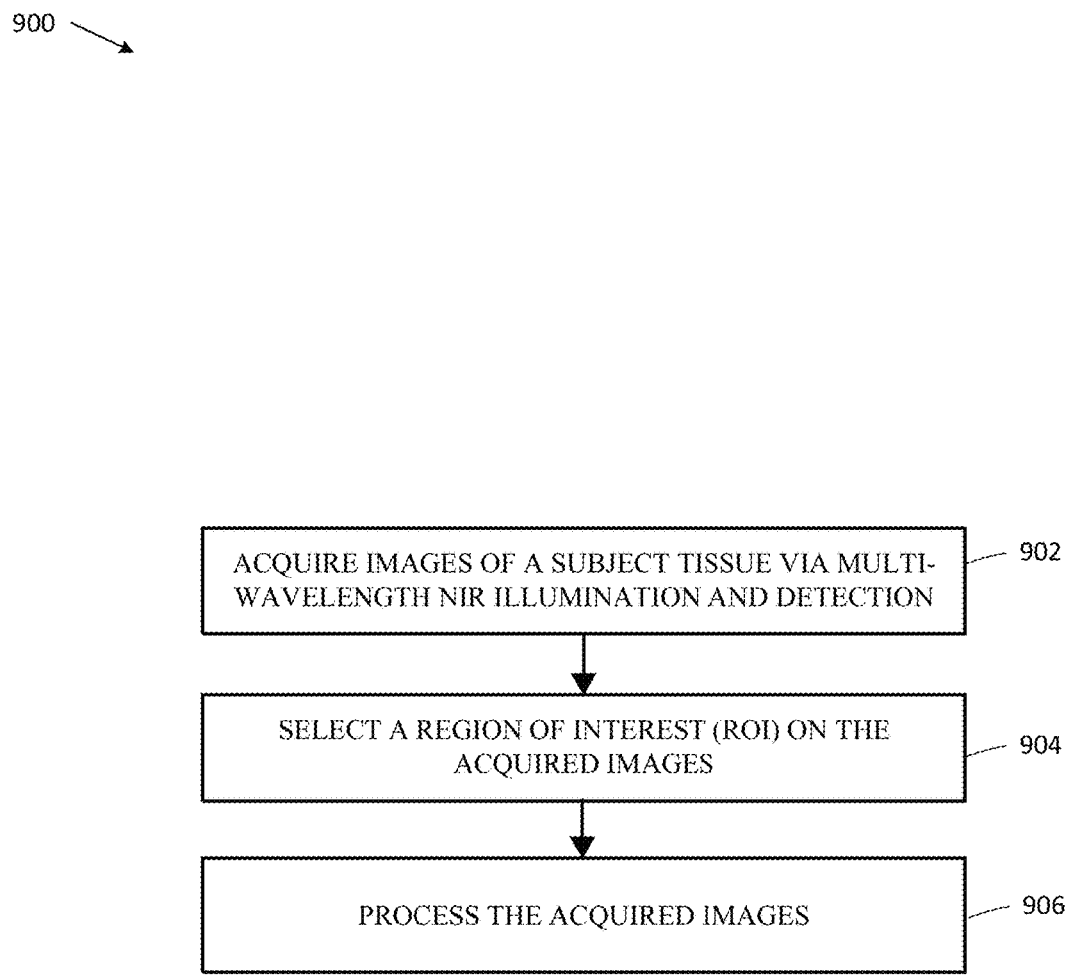
FIG. 9 illustrates an example method 900 for an overall NIR imaging process in accordance with an exemplary aspect of the present disclosure.

FIG. 9 illustrates an example method 900 in accordance with an exemplary aspect of the present disclosure. In an embodiment, method 900 may be implemented by any suitable device, such as control module 102, for example, as shown in FIG. 1. In an embodiment, method 800 may be performed by one or more processors, modules, algorithms, applications, and/or routines, such as any suitable portion of control module 102 (e.g., processor 104) working in conjunction with one or more of image processing/storage module 116, image alignment/ROI selection module 118, subtraction analysis module 124, frequency analysis module 126, spatio-temporal analysis module 128 and/or hemodynamic concentration calculation module 130, for example, as shown in FIG. 1. In an embodiment, method 900 may be performed, for example, on the data represented by the selected ROI from method 500 (block 510) as discussed with reference to FIG. 5.

Method 900 may start when one or more processors receive one or more NIR intensity image samples corresponding to one or more sampled tissue images via multi-wavelength NIR illumination and detection (block 902). These images may be acquired, for example, via communication unit 110 of control module 102 from probe assembly 150, as shown in FIG. 1 (block 902).

Method 900 may include one or more processors selecting a region of interest (ROI) on the acquired images (block 904). In an embodiment, method 900 may include the manual or automatic selection of an ROI (block 904). In manual ROI selection embodiments, method 900 may include a user cropping or otherwise selecting the ROI (block 904) from the acquired images (block 902). In automatic ROI selection embodiments, method 900 may include one or more processors using any suitable image recognition techniques to identify the ROI from characteristics of the acquired images (block 904).

Method 900 may include one or more processors processing the acquired images (block 906). This processing may include, for example, producing a hemodynamic map, extracting frequency components, determining spatio-temporal features, correcting for motion artifacts, and/or masking and/or removing noise (block 906).

The embodiments described herein utilize NIR light to determine hemodynamic information in an image tissue sample. As previously discussed, specific NIR wavelengths, or wavelength ranges, may be particularly useful for this purpose. However, these embodiments also include extracting other types of tissue information from the image tissue samples aside from the hemodynamic information. In such a case, the NIR wavelengths may be adjusted as needed depending on the particular application and/or the desired tissue information that is sought to be extracted.

Although FIG. 1 illustrates several hardware and software modules having their associated functions described herein, it should be understood that embodiments may include the functionality of one or more of these modules but not others. For example, if only one post-processing analysis is selected, then the remaining modules including instructions for the other post-processing analyses are not required, and may be omitted.

Furthermore, the flow charts shown in FIGS. 5-9 are provided for exemplary and illustrative purposes. The co-registration process, any of the pre-processing analyses (e.g., image alignment), and/or any of the post-processing analyses discussed herein (e.g., subtraction analysis, frequency analysis, spatio-temporal analysis, etc.) may be performed in any suitable order from one another and/or may be applied to the NIR intensity image sample data before or after being converted to hemodynamic data.

In addition, the various blocks included throughout the flow charts may be optional based upon a selected pre or post-processing analysis. For example, a user may utilize system 100 without co-registering the images, without applying quantum efficiency compensation (e.g., if only one NIR wavelength is used), without sorting the NIR image data by wavelength (e.g., if only one NIR wavelength is used), etc.

Throughout this specification, plural instances may implement components, operations, or structures described as a single instance. Although individual operations of one or more methods are illustrated and described as separate operations, one or more of the individual operations may be performed concurrently, and nothing requires that the operations be performed in the order illustrated. Structures and functionality presented as separate components in example configurations may be implemented as a combined structure or component. Similarly, structures and functionality presented as a single component may be implemented as separate components. These and other variations, modifications, additions, and improvements fall within the scope of the subject matter herein.

Additionally, certain embodiments are described herein as including logic or a number of routines, subroutines, applications, or instructions. These may constitute either software (e.g., code embodied on a machine-readable medium or in a transmission signal) or hardware. In hardware, the routines, etc., are tangible units capable of performing certain operations and may be configured or arranged in a certain manner. In example embodiments, one or more computer systems (e.g., a standalone, client or server computer system) or one or more hardware modules of a computer system (e.g., a processor or a group of processors) may be configured by software (e.g., an application or application portion) as a hardware module that operates to perform certain operations as described herein, which may include operations such as data acquisition, storage, post-processing, etc.

In various embodiments, a hardware module may be implemented mechanically or electronically. For example, a hardware module may comprise dedicated circuitry or logic that is permanently configured (e.g., as a special-purpose processor, such as a field programmable gate array (FPGA) or an application-specific integrated circuit (ASIC)) to perform certain operations. A hardware module may also comprise programmable logic or circuitry (e.g., as encompassed within a general-purpose processor or other programmable processor) that is temporarily configured by software to perform certain operations. It will be appreciated that the decision to implement a hardware module mechanically, in dedicated and permanently configured circuitry, or in temporarily configured circuitry (e.g., configured by software) may be driven by cost and time considerations.

Accordingly, the term "hardware module" should be understood to encompass a tangible entity, be that an entity that is physically constructed, permanently configured (e.g., hardwired), or temporarily configured (e.g., programmed) to operate in a certain manner or to perform certain operations described herein. Considering embodiments in which hardware modules are temporarily configured (e.g., programmed), each of the hardware modules need not be configured or instantiated at any one instance in time. For example, where the hardware modules comprise a general-purpose processor configured using software, the general-purpose processor may be configured as respective different hardware modules at different times. Software may accordingly configure a processor, for example, to constitute a particular hardware module at one instance of time and to constitute a different hardware module at a different instance of time.

Hardware modules can provide information to, and receive information from, other hardware modules. Accordingly, the described hardware modules may be regarded as being communicatively coupled. Where multiple of such hardware modules exist contemporaneously, communications may be achieved through signal transmission (e.g., over appropriate circuits and buses) that connects the hardware modules. In embodiments in which multiple hardware modules are configured or instantiated at different times, communications between such hardware modules may be achieved, for example, through the storage and retrieval of information in memory structures to which the multiple hardware modules have access. For example, one hardware module may perform an operation and store the output of that operation in a memory device to which it is communicatively coupled. A further hardware module may then, at a later time, access the memory device to retrieve and process the stored output. Hardware modules may also initiate communications with input or output devices, and can operate on a resource (e.g., a collection of information).

The various operations of the example methods described herein may be performed, at least partially, by one or more processors that are temporarily configured (e.g., by software) or permanently configured to perform the relevant operations. Whether temporarily or permanently configured, such processors may constitute processor-implemented modules that operate to perform one or more operations or functions. The modules referred to herein may, in some example embodiments, comprise processor-implemented modules.

Similarly, the methods or routines described herein may be at least partially processor-implemented. For example, at least some of the operations of a method may be performed by one or more processors or processor-implemented hardware modules. The performance of certain of the operations may be distributed among the one or more processors, not only residing within a single machine, but also deployed across a number of machines. In some example embodiments, the processor or processors may be located in a single location (e.g., within a home environment, an office environment or as a server farm), while in other embodiments the processors may be distributed across a number of locations.

The performance of certain of the operations may be distributed among the one or more processors, not only residing within a single machine, but also deployed across a number of machines. In some example embodiments, the one or more processors or processor-implemented modules may be located in a single geographic location (e.g., within a home environment, an office environment, or a server farm). In other example embodiments, the one or more processors or processor-implemented modules may be distributed across a number of geographic locations.

Unless specifically stated otherwise, discussions herein using words such as "processing," "computing," "calculating," "determining," "presenting," "displaying," or the like may refer to actions or processes of a machine (e.g., a computer) that manipulates or transforms data represented as physical (e.g., electronic, magnetic, or optical) quantities within one or more memories (e.g., volatile memory, non-volatile memory, or a combination thereof), registers, or other machine components that receive, store, transmit, or display information.

As used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

Some embodiments may be described using the expression "coupled" and "connected" along with their derivatives. For example, some embodiments may be described using the term "coupled" to indicate that two or more elements are in direct physical or electrical contact. The term "coupled," however, may also mean that two or more elements are not in direct contact with each other, but yet still cooperate or interact with each other. The embodiments are not limited in this context.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

In addition, use of the "a" or "an" are employed to describe elements and components of the embodiments herein. This is done merely for convenience and to give a general sense of the description. This description, and the claims that follow, should be read to include one or at least one and the singular also includes the plural unless it is obvious that it is meant otherwise.

This detailed description is to be construed as an example only and does not describe every possible embodiment, as describing every possible embodiment would be impractical, if not impossible. One could implement numerous alternate embodiments, using either current technology or technology developed after the filing date of this application.

The particular features, structures, or characteristics of any specific embodiment may be combined in any suitable manner and in any suitable combination with one or more other embodiments, including the use of selected features without corresponding use of other features. In addition, many modifications may be made to adapt a particular application, situation or material to the essential scope and spirit of the present invention. It is to be understood that other variations and modifications of the embodiments of the present invention described and illustrated herein are possible in light of the teachings herein and are to be considered part of the spirit and scope of the present invention. By way of example, and not limitation, the present disclosure contemplates at least the following aspects:

1. A system comprising:
   a hand-held probe assembly comprising:
   a probe body;
   a detector assembly comprising a detector configured to capture an area of an image in the near-infrared spectrum; and
   a source assembly comprising a near infrared light source movable relative to the detector such that the probe can perform both reflectance and trans-illumination measurements; and
   a control module configured to capture dynamic near-infrared signals at a plurality of wavelengths and to obtain real-time dynamic hemodynamic signals.

2. The system of aspect 1, wherein the control module comprises one or more drivers for controlling the source assembly and one or more hardware or software modules for controlling the detector assembly.

3. The system of aspects 1 or 2, further comprising a tracking module configured to track a tracking target disposed on the probe assembly, and
   wherein the control module comprises one or more hardware or software modules for receiving and processing data from the tracking module.

4. The system of any one of the preceding aspects, wherein the source assembly includes a plurality of infrared light sources at different wavelengths and wherein the control module is further configured to control the source assembly to multiplex the plurality of infrared light sources at a pre-determined frequency to create multiplexed source illumination that is synchronized with the detector.

5. The system of any one of the preceding aspects, wherein the control module is configured to track the movement of the hand-held probe assembly using the tracking target.

6. The system of any one of the preceding aspects, wherein the control module is configured to capture a plurality of images and to align the captured images.

7. The system of any one of the preceding aspects, wherein the system is configured to perform reflectance and trans-illumination imaging.

8. The system of any one of the preceding aspects, wherein the source assembly comprises a 690 nm source and an 830 nm source.

9. The system of any one of the preceding claims, wherein the source assembly comprises a first source having a wavelength between 670 nm and 710 nm, inclusive, and a second source having a wavelength between 810 nm and 850 nm, inclusive.

10. The system of any one of the preceding aspects, wherein the system is operable to determine a change in oxy-hemoglobin (HbO) concentration in an imaged tissue region, a change in deoxy-hemoglobin (HbR) concentration in the imaged tissue region, and a change in total hemoglobin (HbT) concentration in the imaged tissue region.

11. The system of any one of the preceding aspects, wherein the detector includes at least one of:
   a CCD detector; and
   a CMOS detector.

12. The system of any one of the preceding aspects, wherein the control module is configured to analyze frequency components to monitor a pulse at any point in an imaged surface.

13. The system of any one of the preceding aspects, wherein the control module is configured to provide histograms of intensity distributions and an equalizer.

14. The system of any one of the preceding aspects, wherein the control module is configured to provide real-time imaging as pictures, static images, or video of hemodynamic changes.

15. The system of any one of the preceding aspects, wherein the control module is configured to extract spatio-temporal features of the dynamic near-infrared signals or the real-time dynamic hemodynamic signals.

16. The system of any one of the preceding aspects, wherein the control module comprises a real-time monitoring subsystem.

17. The system of any one of the preceding aspects, wherein the control module comprises a subsystem configured to perform a region-of-interest based analysis in which a specific region of interest is examined to perform one or more of the following:
   extraction of NIR intensity time series information from selected ROI positions;
   calculation of changes in HbO, HbT, and/or HbR using NIR intensity time series information; and/or
   analysis of frequency to determine hemodynamic response.

18. The system of any one of the preceding aspects, wherein the control module comprises a subsystem operable to perform a map based analysis in which changes in HbO, changes in HbR, and/or changes in HbT are on mapped on a an NIR intensity background image to provide a hemodynamic response activity map.

19. The system of any one of the preceding aspects, wherein the control module is configured to perform masking to remove unwanted regions around a region of interest to increase image contrast.

20. A hand-held probe assembly for performing contact and non-contact imaging of biological tissue, comprising:
   a controller configured to cause a near-infrared (NIR) light source to illuminate
   the biological tissue with two different NIR light wavelengths as part of a time-division multiplexed schedule;
   a detector assembly configured to receive NIR light from the NIR illuminated
   biological tissue at each of the two NIR wavelengths in accordance with the time-division multiplexed schedule, to convert the captured NIR light to NIR signals, and to generate a plurality of NIR image samples at each of the two NIR wavelengths based upon the NIR signals; and
   a control module configured to sort the plurality of NIR image samples according to each respective NIR wavelength and to process the NIR signals corresponding to each of the plurality of NIR image samples to generate a hemodynamic response activity map of the biological tissue.

21. The hand-held probe assembly of aspect 20, wherein the control module is further configured to process the NIR signals corresponding to each of the plurality of NIR image samples to generate real-time dynamic hemodynamic signals.

22. The hand-held probe assembly of either aspect 20 or 21, wherein the control module is further configured to process the real-time dynamic hemodynamic signals corresponding to each of the plurality of NIR image samples to perform one or more of:
   subtraction analysis;
   extraction of the NIR signal frequency components; and
   determination of spatio-temporal features of the NIR signal frequency components.

23. The hand-held probe assembly of any one of aspects 20 through 22, wherein the control module is further configured to process the NIR signals corresponding to each of the plurality of NIR image samples to perform one or more of:

subtraction analysis;

extraction of the NIR signal frequency components; and determination of spatio-temporal features of the NIR signal frequency components.

24. The hand-held probe assembly of any one of aspects 20 through 23, wherein the real-time dynamic hemodynamic signals include data indicative of changes in oxy-hemoglobin (HbO), deoxy-hemoglobin (HbR), and/or total hemoglobin (HbT) in the biological tissue.

25. The hand-held probe assembly of any one of aspects 20 through 24, further comprising:

a tracking target configured to generate positional data indicative of a relative position of the hand-held probe assembly to the NIR light source while the plurality of NIR image samples are being generated, and wherein the control module is further configured to co-register the plurality of NIR image samples with an image of the biological tissue using the positional data.

26. The hand-held probe assembly of any one of aspects 20 through 25, wherein the detector assembly is configured to receive the NIR light from the NIR illuminated biological tissue in accordance with one or more of:

NIR light attenuated through the biological tissue from the NIR light source being adjacent to the biological tissue;

NIR light transmitted through the biological tissue from the biological tissue being placed between the source assembly and the NIR light source; and NIR light reflected off of the biological tissue.

27. The hand-held probe assembly of any one of aspects 20 through 26, wherein the control module is further configured to perform masking to remove unwanted regions around a region of interest to increase image contrast of one or more of the plurality of NIR image samples.

28. An image processing method comprising:

acquiring images of a subject tissue using a hand-held probe assembly, the probe assembly configured to perform multi-wavelength near infrared (NIR) illumination and detection;

selecting a region of interest on the acquired images;

processing the images using the dynamic near-infrared signals or the real-time dynamic hemodynamic signals to perform one or more of:

producing a hemodynamic response activity map;

producing an NIR image;

performing subtraction analysis;

extracting frequency components;

determining spatio-temporal features;

correcting for motion artifacts; and masking and/or removing noise.

29. The method of aspect 28, further comprising:

automating the acquisition of the images and controlling, in real-time, the multi-wavelength illumination and detection.

30. The method of either aspect 28 or 29, further comprising:

obtaining hemodynamic data as static data or in real time.

31. The method of any one of aspects 28 through 30, wherein obtaining hemodynamic data comprises:

obtaining data related to changes in oxy-hemoglobin (HbO), deoxy-hemoglobin (HbR), and/or total hemoglobin (HbT).

32. The method of any one of aspects 28 through 31, wherein extracting frequency components comprises:

extracting a frequency component of the dynamic near-infrared signals or the dynamic real-time hemodynamic signals used to determine a pulse over an imaged area.

33. The method of any one of any one of aspects 28 through 32, wherein determining spatio-temporal features comprises:

extracting a spatio-temporal feature from the dynamic near-infrared signals or the dynamic real-time hemodynamic signals.

34. The method of any one of any one of aspects 28 through 33, wherein correcting for motion artifacts comprises:

performing realignment of the acquired images.

35. The method of claim 28, further comprising:

one or more of the following prior to processing the images:

performing image alignment; and cropping an area common to a plurality of images.

36. The method of any one of any one of aspects 28 through 35, wherein determining spatio-temporal features comprises:

calculating an optical density;

calculating a change in hemodynamic concentration; and performing spatial-temporal analysis.

37. The method of any one of aspects 28 through 36, wherein determining the spatio-temporal feature from the dynamic near-infrared signals or the dynamic real-time hemodynamic signals performing spatial-temporal analysis comprises:

extracting spatial-temporal signal components;

determining temporal features; and performing image reconstruction.

38. The method of any one of aspects 28 through 37, wherein performing extracting frequency components comprises:

performing a Fourier Transform on the dynamic near-infrared signals or the dynamic real-time hemodynamic signals to generate frequency components; and mapping the to generate frequency components to the NIR image.

39. The method of any one of aspects 28 through 38, further comprising:

providing a histogram of an intensity distribution.

40. The method of any one of claims 28 through 39, further comprising:

providing an equalizer with a histogram of intensity distribution.

41. The method of any one of aspects 28 through 40, wherein acquiring images of the subject tissue comprises:

acquiring images without the probe assembly being in contact with the subject tissue.

42. The method of any one of aspects 28 through 41, wherein acquiring images of the subject tissue comprises acquiring images with the probe assembly being in contact with the subject tissue.

43. The method of any one of aspects 28 through 42, further comprising:

tracking the relative positions of the hand-held probe assembly and the subject tissue while acquiring the images of the subject tissue.

44. The method of any one of aspects 28 through 43, further comprising:

performing real-time imaging of hemodynamic changes in oxy-hemoglobin (HbO), deoxy-hemoglobin (HbR), and/or total hemoglobin (HbT).

What is claimed:

1. A system comprising:
a hand-held probe assembly comprising:
a probe body;
a detector assembly comprising a detector configured to capture an area of an image in the near-infrared spectrum; and
a source assembly comprising a near infrared light source movable relative to the detector and configured to obtain both reflectance and trans-illumination measurements depending upon the position of the near infrared light source relative to the detector; and
a control module configured to capture dynamic near-infrared signals at a plurality of wavelengths and to obtain real-time dynamic hemodynamic signals.

2. The system of claim 1, wherein the control module comprises one or more drivers for controlling the source assembly and one or more hardware or software modules for controlling the detector assembly.

3. The system of claim 1, further comprising a tracking module configured to track a tracking target disposed on the hand-held probe assembly, and wherein the control module comprises one or more hardware or software modules for receiving and processing data from the tracking module.

4. The system of claim 1, wherein the source assembly includes a plurality of infrared light sources at different wavelengths and wherein the control module is further configured to control the source assembly to multiplex the plurality of infrared light sources at a pre-determined frequency to create multiplexed source illumination that is synchronized with the detector.

5. The system of claim 3, wherein the control module is configured to communicate with the probe assembly to receive and process data from the tracking target to track the movement of the hand-held probe.

6. The system of claim 1, wherein the control module is configured to capture a plurality of images and to align the captured images.

7. The system of claim 1, wherein the control module is configured to receive data from the probe assembly to obtain the reflectance and trans-illumination imaging measurements.

8. The system of claim 1, wherein the source assembly comprises a 690 nm source and an 830 nm source.

9. The system of claim 1, wherein the source assembly comprises a first source having a wavelength between 670 nm and 710 nm, inclusive, and a second source having a wavelength between 810 nm and 850 nm, inclusive.

10. The system of claim 1, wherein the control module is configured to analyze the dynamic near-infrared signals to obtain a change in oxy-hemoglobin (HbO) concentration in an imaged tissue region, a change in deoxy-hemoglobin (HbR) concentration in the imaged tissue region, and a change in total hemoglobin (HbT) concentration in the imaged tissue region.

11. The system of claim 1, wherein the detector includes at least one of:
a CCD detector; and
a CMOS detector.

12. The system of claim 1, wherein the control module is configured to analyze frequency components to monitor a pulse at any point in an imaged surface.

13. The system of claim 1, wherein the control module is configured to provide histograms of intensity distributions and an equalizer.

14. The system of claim 1, wherein the control module is configured to provide real-time imaging as pictures, static images, or video of hemodynamic changes.

15. The system of claim 1, wherein the control module is configured to extract spatio-temporal features of the dynamic near-infrared signals or the real-time dynamic hemodynamic signals.

16. The system of claim 1, wherein the control module comprises a real-time monitoring subsystem.

17. The system of claim 1, wherein the control module comprises a subsystem configured to perform a region-of-interest based analysis in which a specific region of interest is examined to perform one or more of the following:
extraction of NIR intensity time series information from selected ROI positions;
calculation of changes in HbO, HbT, and/or HbR using NIR intensity time series information; and/or
analysis of the dynamic near-infrared signals at the plurality of wavelengths to determine hemodynamic response.

18. The system of claim 1, wherein the control module comprises a subsystem operable to perform a map based analysis in which changes in HbO, changes in HbR, and/or changes in HbT are mapped on an NIR intensity background image to provide a hemodynamic response activity map.

19. The system of claim 1, wherein the control module is configured to perform masking to remove unwanted regions around a region of interest to increase image contrast.

20. A computer-implemented method, comprising:
capturing, via a detector assembly including a detector, an area of an image in the near-infrared spectrum;
obtaining, via a source assembly that includes a near infrared light source movable relative to the detector, both (i) reflectance, and (ii) trans-illumination measurements depending upon a position of the near infrared light source relative to the detector; and
capturing, via a control module, dynamic near-infrared signals at a plurality of wavelengths to obtain real-time dynamic hemodynamic signals.

21. The computer-implemented method of claim 20, further comprising:
controlling, via the control module, the source assembly and the detector assembly.

22. The computer-implemented method of claim 20, further comprising:
tracking, via a tracking module, a tracking target disposed on a hand-held probe assembly that includes the detector assembly and the source assembly, and
processing, via the control module, data received from the tracking module.

23. The computer-implemented method of claim 20, further comprising:
controlling, via the control module, the source assembly to multiplex a plurality of infrared light sources included as part of the source assembly at a pre-determined frequency to create multiplexed source illumination that is synchronized with the detector.

24. The computer-implemented method of claim 22, further comprising:
communicating, via the control module, with the probe assembly to receive and process data from the tracking target to track the movement of the hand-held probe.

25. The computer-implemented method of claim 20, further comprising:
capturing, via the control module, a plurality of images; and
aligning, via the control module, the captured images.

26. The computer-implemented method of claim 20, further comprising:
receiving, via the control module, data from the probe assembly to obtain one or more of the reflectance and trans-illumination imaging measurements.

27. The computer-implemented method of claim 20, wherein the act of obtaining the one or more of the reflectance and trans-illumination measurements includes obtaining the one or more of the reflectance and trans-illumination measurements via the source assembly that includes a 690 nm source and an 830 nm source.

28. The computer-implemented method of claim 20, wherein the act of obtaining the one or more of the reflectance and trans-illumination measurements includes obtaining the one or more of the reflectance and trans-illumination measurements via the source assembly that includes a first source having a wavelength between 670 nm and 710 nm, inclusive, and a second source having a wavelength between 810 nm and 850 nm, inclusive.

29. The computer-implemented method of claim 20, further comprising:
analyzing, via the control module, the dynamic near-infrared signals to obtain a change in oxy-hemoglobin (HbO) concentration in an imaged tissue region, a change in deoxy-hemoglobin (HbR) concentration in the imaged tissue region, and a change in total hemoglobin (HbT) concentration in the imaged tissue region.

30. The computer-implemented method of claim 20, wherein the act of capturing the area of the image in the near-infrared spectrum includes capturing the area of the image via a detector that includes least one of:
a CCD detector; and
a CMOS detector.

31. The computer-implemented method of claim 20, further comprising:
analyzing, via the control module, frequency components to monitor a pulse at any point in an imaged surface.

32. The computer-implemented method of claim 20, further comprising:
providing, via the control module, histograms of intensity distributions and an equalizer.

33. The computer-implemented method of claim 20, further comprising:
providing, via the control module, real-time imaging as pictures, static images, or video of hemodynamic changes.

34. The computer-implemented method of claim 20, further comprising:
extracting, via the control module, spatio-temporal features of the dynamic near-infrared signals or the real-time dynamic hemodynamic signals.

35. The computer-implemented method of claim 20, further comprising:
executing, via the control module, a region-of-interest based analysis in which a specific region of interest is examined to perform one or more of the following:
extraction of NIR intensity time series information from selected ROI positions;
calculation of changes in HbO, HbT, and/or HbR using NIR intensity time series information; and/or
analysis of the dynamic near-infrared signals at the plurality of wavelengths to determine hemodynamic response.

36. The computer-implemented method of claim 20, further comprising:
performing, via the control module, a map-based analysis in which changes in HbO, changes in HbR, and/or changes in HbT are mapped on an NIR intensity background image to provide a hemodynamic response activity map.

37. The computer-implemented method of claim 20, further comprising:
performing, via the control module, masking to remove unwanted regions around a region of interest to increase image contrast.

* * * * *